United States Patent
Vijayachandran

(10) Patent No.: US 11,986,215 B2
(45) Date of Patent: May 21, 2024

(54) UNIVERSAL SIZE MULTI-WALLED ELASTOMER CANNULA DEPTH LIMITER

(71) Applicant: Cilag GmbH International, Zug (CH)

(72) Inventor: Sajayesh Vijayachandran, Kannur (IN)

(73) Assignee: Cilag GmbH International, Zug (CH)

( * ) Notice: Subject to any disclaimer, the term of this patent is extended or adjusted under 35 U.S.C. 154(b) by 270 days.

(21) Appl. No.: 17/213,409

(22) Filed: Mar. 26, 2021

(65) Prior Publication Data

US 2021/0338282 A1    Nov. 4, 2021

(30) Foreign Application Priority Data

May 1, 2020 (IN) .............................. 202011018668

(51) Int. Cl.
*A61B 17/34* (2006.01)
*A61B 90/00* (2016.01)

(52) U.S. Cl.
CPC ...... *A61B 17/3494* (2013.01); *A61B 17/3423* (2013.01); *A61B 90/03* (2016.02); *A61B 2090/036* (2016.02)

(58) Field of Classification Search
CPC ................ A61B 90/03; A61B 17/3423; A61B 2090/036; A61B 17/3494; A61B 17/3462;
(Continued)

(56) References Cited

U.S. PATENT DOCUMENTS

| 3,817,251 A | 6/1974 | Hasson |
| 3,896,527 A | 7/1975 | Miller et al. |

(Continued)

FOREIGN PATENT DOCUMENTS

| AU | 702882 B2 | 3/1993 |
| CN | 106344126 B | 2/2019 |

(Continued)

OTHER PUBLICATIONS

International Search Report and Written Opinion dated Jul. 22, 2021, for International Application No. PCT/EP2021/061421, 15 pages.

(Continued)

*Primary Examiner* — Tan-Uyen T Ho
*Assistant Examiner* — Bridget E. Rabaglia
(74) *Attorney, Agent, or Firm* — Frost Brown Todd LLP

(57) ABSTRACT

A depth limiter that is configured to couple with a cannula tube of a trocar having a tube cross dimension. The depth limiter includes an outer frame portion and an inner gripping portion housed within the outer frame portion. The inner gripping portion includes a plurality of lobes flexible relative to each other between a relaxed configuration and at least a first flexed configuration. In the relaxed configuration the plurality of lobes collectively form a first effective cross dimension configured to be less than the tube cross dimension. In the first flexed configuration the plurality of lobes collectively form a second effective cross dimension greater than the first effective cross dimension and configured to be equal to the tube cross dimension such that the second effective cross dimension is sized to restrict axial movement of the depth limiter relative to the cannula tube of the trocar.

20 Claims, 18 Drawing Sheets

(58) Field of Classification Search
CPC .......... A61B 17/3469; A61B 2017/347; A61B 17/3498; A61B 2017/3492; A61B 17/0293; A61B 17/3431; A61B 2017/00265; A61B 1/00131; A61B 1/00133; A61B 1/00135; A61B 1/0014; A61B 1/00154; A61B 1/00147; A61B 5/150175; A61B 5/150183; A61B 5/15019; A61B 5/150198; A61M 25/02; Y10S 128/26

See application file for complete search history.

(56) References Cited

U.S. PATENT DOCUMENTS

| | | | |
|---|---|---|---|
| 4,699,616 | A | 10/1987 | Nowak et al. |
| 5,002,557 | A | 3/1991 | Hasson |
| 5,147,316 | A | 9/1992 | Castillenti |
| 5,215,531 | A | 6/1993 | Maxson et al. |
| D338,270 | S | 8/1993 | Stephens et al. |
| 5,256,147 | A | 10/1993 | Vidal et al. |
| 5,257,975 | A | 11/1993 | Foshee |
| 5,263,939 | A | 11/1993 | Wortrich |
| 5,267,970 | A | 12/1993 | Chin et al. |
| 5,290,249 | A | 3/1994 | Foster et al. |
| 5,364,372 | A | 11/1994 | Danks et al. |
| D354,562 | S | 1/1995 | Medema |
| 5,540,675 | A | 7/1996 | Hasson |
| 5,697,913 | A | 12/1997 | Sierocuk et al. |
| 5,792,135 | A | 8/1998 | Madhani et al. |
| 5,800,451 | A | 9/1998 | Buess et al. |
| 5,817,061 | A | 10/1998 | Goodwin et al. |
| 5,833,666 | A | 11/1998 | Davis et al. |
| 5,836,913 | A | 11/1998 | Orth et al. |
| 5,855,566 | A | 1/1999 | Dunlap et al. |
| 5,951,588 | A | 9/1999 | Moenning |
| 5,957,888 | A | 9/1999 | Hinchcliffe |
| 6,432,085 | B1 | 8/2002 | Stellon et al. |
| 6,451,041 | B1 | 9/2002 | Moenning et al. |
| 6,620,173 | B2 | 9/2003 | Gerbi et al. |
| 6,632,197 | B2 | 10/2003 | Lyon |
| 6,638,265 | B1 | 10/2003 | Ternamian |
| 6,652,490 | B2 | 11/2003 | Howell |
| 6,808,492 | B2 | 10/2004 | Snyder |
| 7,235,064 | B2 | 6/2007 | Hopper et al. |
| 7,473,220 | B2 | 1/2009 | Francese et al. |
| 7,981,092 | B2 | 7/2011 | Duke |
| 8,147,453 | B2 | 4/2012 | Albrecht et al. |
| 8,226,553 | B2 | 7/2012 | Shelton, IV et al. |
| 8,251,900 | B2 | 8/2012 | Ortiz et al. |
| 8,287,503 | B2 | 10/2012 | Albrecht et al. |
| 8,479,969 | B2 | 7/2013 | Shelton, IV |
| 8,568,362 | B2 | 10/2013 | Moreno, Jr. et al. |
| 8,573,465 | B2 | 11/2013 | Shelton, IV |
| 8,579,807 | B2 | 11/2013 | Moreno, Jr. et al. |
| 8,636,686 | B2 | 1/2014 | Minnelli et al. |
| 8,690,831 | B2 | 4/2014 | Duke |
| 8,783,541 | B2 | 7/2014 | Shelton, IV et al. |
| 8,800,838 | B2 | 8/2014 | Shelton, IV |
| 8,821,527 | B2 | 9/2014 | Farnan et al. |
| 8,939,946 | B2 | 1/2015 | Albrecht et al. |
| 9,004,545 | B2 | 4/2015 | Whitaker et al. |
| 9,259,238 | B2 | 2/2016 | Albrecht et al. |
| 9,289,200 | B2 | 3/2016 | Dang et al. |
| 9,522,265 | B2 | 12/2016 | Pravong et al. |
| 9,668,723 | B2 * | 6/2017 | Keating .............. A61B 17/0469 |
| 9,675,379 | B2 | 6/2017 | Kucklick |
| 10,327,805 | B2 | 6/2019 | Hibner et al. |
| 10,327,809 | B2 | 6/2019 | Buyda et al. |
| 10,576,259 | B2 | 3/2020 | Stafford |
| 10,792,069 | B2 | 10/2020 | Hall et al. |
| 10,820,924 | B2 | 11/2020 | Hall et al. |
| 11,359,751 | B2 | 6/2022 | White et al. |
| 11,712,267 | B2 | 8/2023 | McLain |
| 2005/0113856 | A1 | 5/2005 | Epstein et al. |
| 2005/0165432 | A1 | 7/2005 | Heinrich |
| 2007/0225643 | A1 | 9/2007 | Hopper et al. |
| 2009/0182282 | A1 | 7/2009 | Okihisa et al. |
| 2010/0010449 | A1 | 1/2010 | Leibowitz et al. |
| 2010/0057010 | A1 | 3/2010 | Göransson |
| 2013/0060084 | A1 | 3/2013 | Fouts et al. |
| 2014/0066953 | A1 | 3/2014 | Keating et al. |
| 2016/0015423 | A1 | 1/2016 | Ravikumar et al. |
| 2017/0245889 | A1 | 8/2017 | Herrell et al. |
| 2017/0311932 | A1 | 11/2017 | Rebellino |
| 2018/0199959 | A1 | 7/2018 | Lee |
| 2018/0206883 | A1 | 7/2018 | McIntyre et al. |
| 2018/0214140 | A1 | 8/2018 | Nock et al. |
| 2019/0000496 | A1 | 1/2019 | Shelton, IV et al. |
| 2019/0083071 | A1 | 3/2019 | Rebellino et al. |
| 2019/0150900 | A1 | 5/2019 | Choung et al. |
| 2019/0254703 | A1 | 8/2019 | Ciampini et al. |
| 2019/0254704 | A1 | 8/2019 | Buyda et al. |
| 2019/0380742 | A1 | 12/2019 | Hall et al. |
| 2020/0205855 | A1 | 7/2020 | Aravalli |
| 2021/0338269 | A1 | 11/2021 | Scott et al. |
| 2021/0338272 | A1 | 11/2021 | Muthuchidambaram et al. |
| 2021/0338273 | A1 | 11/2021 | Vijayachandran et al. |
| 2021/0338274 | A1 | 11/2021 | Scott et al. |
| 2021/0338275 | A1 | 11/2021 | Vijayachandran |
| 2021/0338276 | A1 | 11/2021 | Scott |
| 2021/0338278 | A1 | 11/2021 | Scott et al. |
| 2021/0338281 | A1 | 11/2021 | Mozloom, Jr. et al. |
| 2021/0338283 | A1 | 11/2021 | McLain |
| 2021/0338371 | A1 | 11/2021 | Harris et al. |

FOREIGN PATENT DOCUMENTS

| | | |
|---|---|---|
| DE | 202007001745 U1 | 4/2007 |
| EP | 2174602 A1 | 4/2010 |
| EP | 3210553 B1 | 10/2019 |
| WO | WO 1999/052457 A1 | 10/1999 |
| WO | WO 2004/032756 A2 | 4/2004 |
| WO | WO 2014/137530 A1 | 9/2014 |
| WO | WO 2015/049391 A1 | 4/2015 |
| WO | WO 2017/132004 A1 | 8/2017 |
| WO | WO 2020/040649 A1 | 2/2020 |

OTHER PUBLICATIONS

International Search Report and Written Opinion dated Aug. 3, 2021, for International Application No. PCT/EP2021/061428, 15 pages.
International Search Report and Written Opinion dated Jul. 16, 2021, for International Application No. PCT/EP2021/061442, 13 pages.
International Search Report and Written Opinion dated Jul. 8, 2021, for International Application No. PCT/EP2021/061447, 15 pages.
International Search Report and Written Opinion dated Jul. 27, 2021, for International Application No. PCT/EP2021/061456, 14 pages.
International Search Report and Written Opinion dated Jul. 13, 2021, for International Application No. PCT/EP2021/061459, 16 pages.
International Search Report and Written Opinion dated Jul. 20, 2021, for International Application No. PCT/EP2021/061466, 17 pages.
International Search Report and Written Opinion dated Jul. 15, 2021, for International Application No. PCT/EP2021/061468, 16 pages.
European Examination Report dated Jul. 26, 2023 for Application No. EP 21722871, 4 pgs.
European Examination Report dated Jul. 20, 2023 for Application No. EP 21723218, 5 pgs.
European Examination Report dated Sep. 15, 2023 for Application No. EP 21722865, 5 pgs.
European Examination Report dated Aug. 10, 2023 for Application No. EP 21722862, 5 pgs.
U.S. Appl. No. 17/213,304.
U.S. Appl. No. 17/213,401.
U.S. Appl. No. 17/213,415.

(56) References Cited

OTHER PUBLICATIONS

U.S. Appl. No. 17/213,431.
U.S. Appl. No. 17/213,434.
U.S. Appl. No. 17/213,508.
U.S. Appl. No. 17/213,518.

* cited by examiner

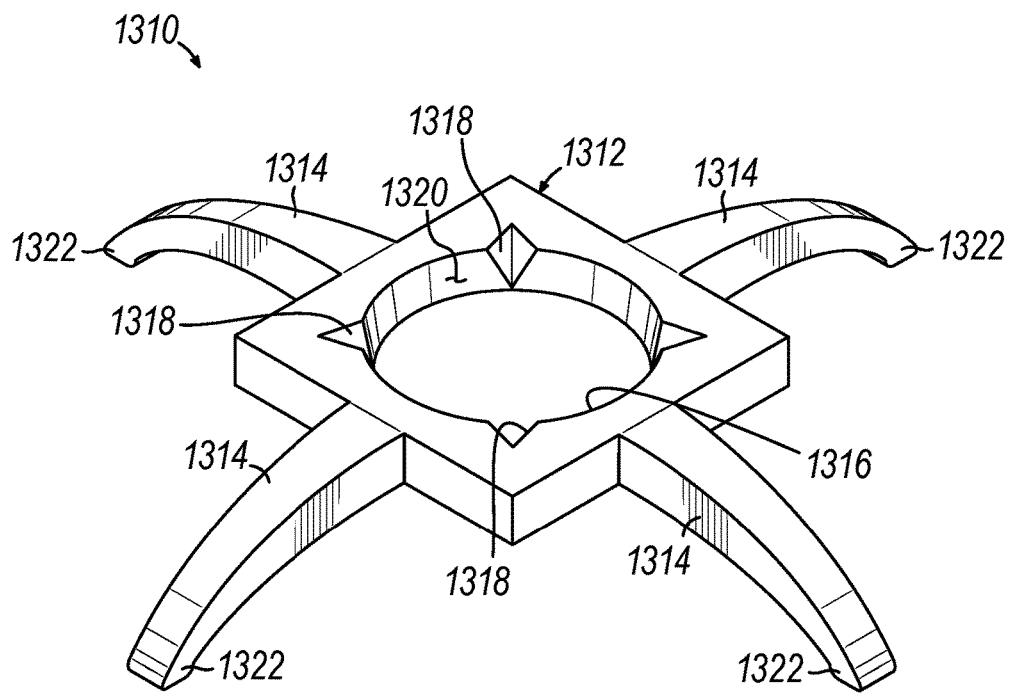
FIG. 15
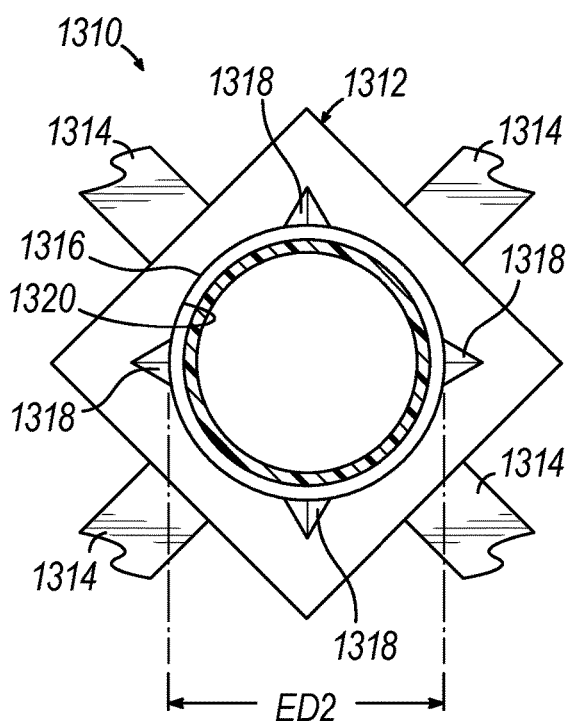 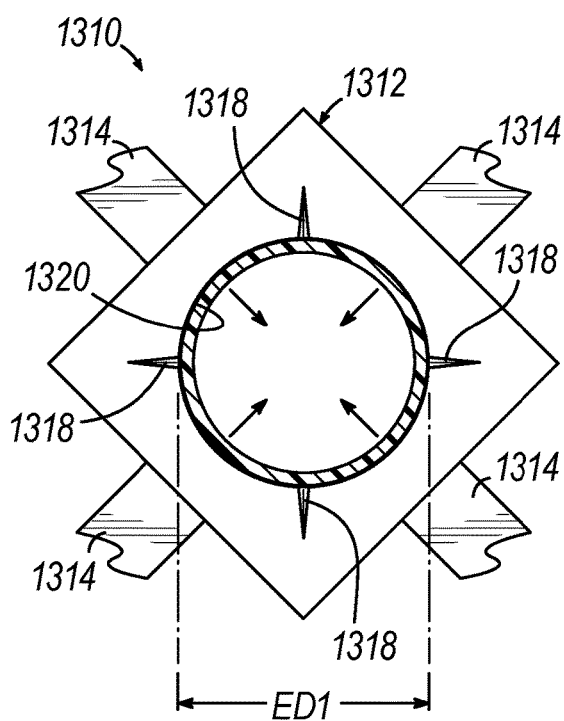
FIG. 16A     FIG. 16B

UNIVERSAL SIZE MULTI-WALLED ELASTOMER CANNULA DEPTH LIMITER

PRIORITY

This application claims priority to Indian Provisional Patent App. No. 202011018668, entitled "Universal Size Multi-Walled Elastomer Cannula Depth Limiter," filed May 1, 2020, the disclosure of which is incorporated by reference herein.

BACKGROUND

Some surgical procedures may require a clinician to access a surgical site via the abdominal cavity of a patient. To gain such access, an opening is first formed through the abdominal wall tissue overlying the abdominal cavity. In some surgical procedures (referred to as "laparoscopic" or "endoscopic" surgeries), a relatively small opening is made through the abdominal wall tissue, and the surgical site is then accessed with elongate instruments inserted through an access device generally referred to as a "trocar" positioned within the opening. Traditional trocars generally include a cannula assembly and an obturator that is removably received within a working channel of the cannula assembly. In use, the obturator is mated with the cannula assembly, and the combined structure (i.e., the trocar) is directed by a clinician downwardly through the abdominal wall of the patient such that the distal ends of the obturator and the cannula assembly extend into the abdominal cavity. The clinician then withdraws the obturator from the cannula assembly so that surgical instruments may be directed downwardly through the working channel of the cannula assembly to access the surgical site.

Merely exemplary versions of trocars, components thereof, and other varieties of surgical access devices are disclosed in U.S. Pat. No. 7,981,092, entitled "Vibratory Trocar," issued Jul. 19, 2011; U.S. Pat. No. 8,226,553, entitled "Access Device with Insert," issued on Jul. 24, 2012; U.S. Pat. No. 8,251,900, entitled "Surgical Access Devices and Methods Providing Seal Movement in Pre-defined Paths," issued on Aug. 28, 2012; U.S. Pat. No. 8,579,807, entitled "Absorbing Fluids in a Surgical Access Device," issued on Nov. 12, 2013; U.S. Pat. No. 8,568,362, entitled "Surgical Access Device with Sorbents," issued on Oct. 29, 2013; U.S. Pat. No. 8,636,686, entitled "Surgical Access Device," issued on Jan. 28, 2014; U.S. Pat. No. 8,690,831, entitled "Gas Jet Fluid Removal in a Trocar," issued on Apr. 8, 2014; and U.S. Pat. Pub. No. 2019/0000496, entitled "Method of Suturing a Trocar Path Incision," published Jan. 3, 2019. The disclosure of each of the above-cited U.S. Patents and Publications is incorporated by reference herein.

While various kinds of surgical instruments, including surgical access devices and end effectors, and other associated components have been made and used, it is believed that no one prior to the inventor(s) has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

FIG. 15 depicts a perspective view of another exemplary depth limiter that includes a hub with notches;

FIG. 16A depicts a top plan view of the depth limiter of FIG. 15 coupled with the cannula tube of the cannula assembly of FIG. 5, where the hub of the depth limiter is in a movable configuration;

FIG. 16B depicts a partial side sectional view of the depth limiter of FIG. 15 coupled with the cannula tube of the cannula assembly of FIG. 5 following detachment and removal of the obturator, where the legs of the depth limiter are in a fixed configuration;

Figure 1:
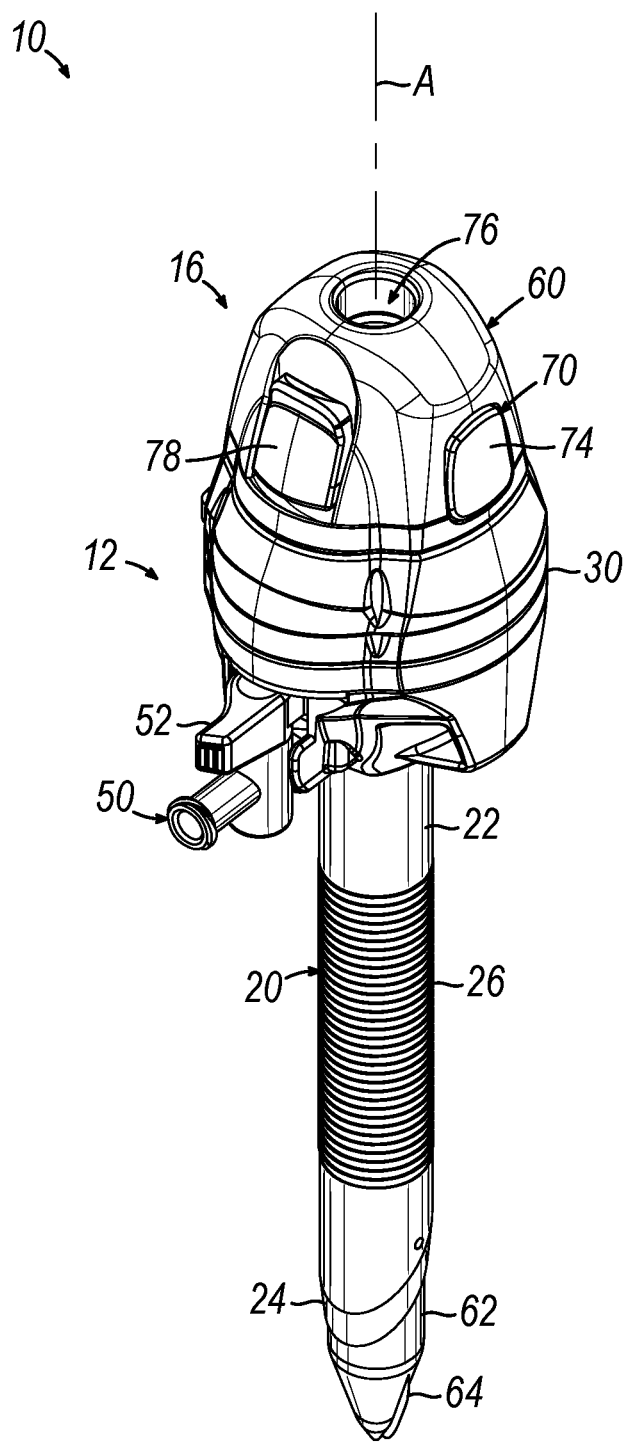
FIG. 1 depicts a perspective view of an exemplary trocar having a cannula assembly and an obturator shown in an assembled state.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

For clarity of disclosure, the terms "proximal" and "distal" are defined herein relative to a surgeon, or other operator, grasping a surgical device. The term "proximal" refers to the position of an element arranged closer to the surgeon, and the term "distal" refers to the position of an element arranged further away from the surgeon. Moreover, to the extent that spatial terms such as "top," "bottom," "upper," "lower," "vertical," "horizontal," or the like are used herein with reference to the drawings, it will be appreciated that such terms are used for exemplary description purposes only and are not intended to be limiting or absolute. In that regard, it will be understood that surgical instruments such as those disclosed herein may be used in a variety of orientations and positions not limited to those shown and described herein.

Furthermore, the terms "about," "approximately," and the like as used herein in connection with any numerical values or ranges of values are intended to encompass the exact value(s) referenced as well as a suitable tolerance that enables the referenced feature or combination of features to function for the intended purpose(s) described herein.

I. Exemplary Single-Use and Reusable Trocars

FIGS. 1-5 depict exemplary surgical access devices in the form of a single-use first trocar (10) and a reusable second trocar (110), each configured to provide surgical site access in a laparoscopic surgical procedure. Each trocar (10, 110) includes a cannula assembly (12, 112) having a working channel (14, 114), and an obturator (16, 116) configured to be removably inserted coaxially into the working channel (14, 114) so that the assembled trocar (10, 110) may be directed distally through the abdominal wall of a patient and into the abdominal cavity, for example as described below in connection with FIGS. 3A-3D.

A. Exemplary Single-Use Trocar

Figure 2:
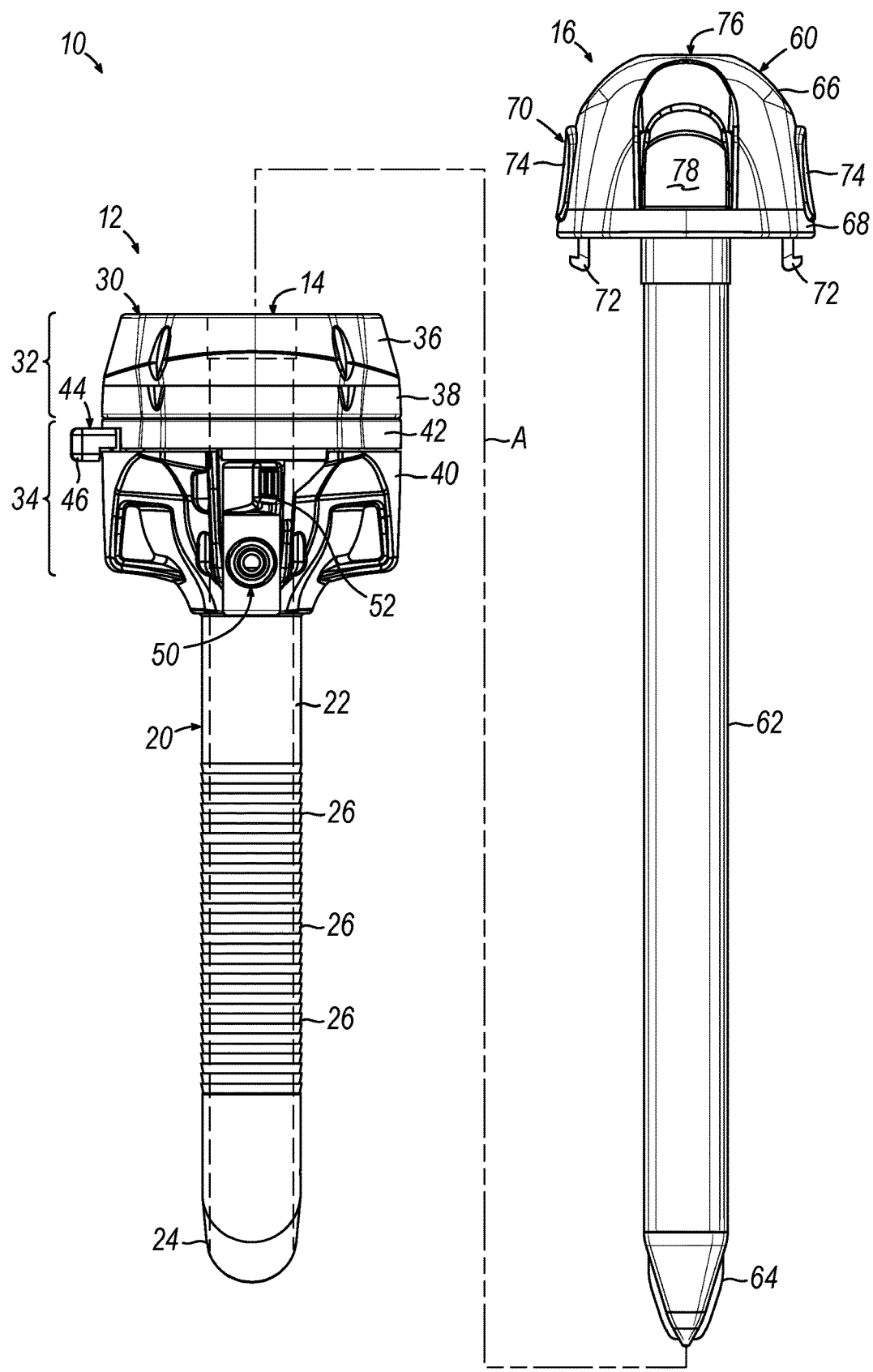
FIG. 2 depicts a side elevational view of the cannula assembly and the obturator of FIG. 1 in a disassembled state.

As shown in FIGS. 1-2, cannula assembly (12) of single-use trocar (10) includes a cannula (20) and a seal housing (30). Cannula (20) and seal housing (30) cooperate to define working channel (14), which extends longitudinally along a central axis (A) of trocar (10). In particular, working channel (14) is defined by a lumen of cannula (20) in communication with a hollow interior of seal housing (30). Cannula assembly (12) is configured to receive elongate surgical instruments distally through working channel (14) to provide access to surgical sites within the abdominal cavity of a patient. As described in greater detail below, seal housing (30) houses a pair of seal structures defining a seal assembly configured to maintain insufflation of the patient's abdominal cavity while permitting passage of surgical instruments and tissue fragments along working channel (14).

Cannula (20) of the present version may include a bell-shaped hub (not shown) at a proximal end thereof, and an elongate cylindrical tube (22) extending distally from the hub and terminating at an angled cannula tip (24). An outer surface of cannula tube (22) includes a plurality of tissue gripping features in the form of annular ribs (26) arranged axially along a medial portion of cannula tube (22). Ribs (26) are configured to grip the layers of abdominal wall tissue through which cannula (20) is inserted, and thereby assist in stabilizing cannula (20) in axial and radial directions while cannula (20) is positioned within the opening formed in the abdominal wall of a patient.

More specifically, tissue gripping ribs (26) of the present example are formed as annular scallops in the sidewall of cannula tube (22) such that each rib (26) tapers radially inwardly in a distal direction from a radially outermost edge of the rib (26). The radially outermost edges of ribs (26) are thus generally flush with the non-ribbed proximal and distal portions of cannula tube (22). The resulting configuration of ribs (26) promotes advancement of cannula tube (22) through tissue layers in a distal direction and resists retraction of cannula tube (22) through the tissue layers in a reverse, proximal direction. Advantageously, this configuration protects against unintended withdrawal of cannula tube (22) from the abdominal wall of patient during a surgical procedure. It will be appreciated, however, that cannula tube (22) may be provided with various other types of tissue gripping features in other versions of trocar (10). For instance, cannula tube (22) may include a tissue gripping feature in the form of one or more helical ribs that extend around at least a medial portion of cannula tube (22), and which may be scalloped similar to ribs (26).

Seal housing (30) of cannula assembly (12) includes a proximal housing portion (32) and a distal housing portion (34) to which proximal housing portion (32) is removably attached. Proximal housing portion (32) includes a proximal head (36) and a distal base (38) secured together. Distal housing portion (34) includes a distal shroud (40) that encircles the proximal hub (not shown) of cannula (20), a cap plate (42) secured to a proximal end of distal shroud (40), and a latch ring (44) rotatably disposed therebetween and having a radially outwardly projecting tab (46). Latch ring (44) is selectively rotatable via tab (46) about the central axis (A) of trocar (10) between a locked position and an unlocked position. In the locked position, latch ring (44) locks proximal housing portion (32) to distal housing portion (34). In the unlocked position, latch ring (44) permits separation of proximal housing portion (32) from distal housing portion (34), for example to directly access a distal seal structure (not shown) housed within distal housing portion (34). In some versions, distal shroud (40) may be formed integrally with the proximal end of cannula tube (22) such that distal shroud (40) is a component of cannula (20).

Though not shown, proximal housing portion (32) houses a proximal (or "outer") seal structure, and distal housing portion (34) houses a distal (or "inner") seal structure, both arranged along the central axis (A) of trocar (10). The proximal and distal seal structures cooperate to define a seal assembly that maintains insufflation of the patient's abdominal cavity during a surgical procedure while permitting passage of surgical instruments and tissue fragments along working channel (14). For instance, the proximal seal structure may include an annular seal member configured to sealingly engage the shaft of a laparoscopic surgical instrument directed through working channel (14). The distal seal structure may include a duckbill seal member configured to maintain working channel (14) in a sealed stated in the absence of a surgical instrument shaft.

Cannula assembly (12) further includes an insufflation port (50) operatively coupled with the proximal end of cannula (20) and having an adjustable valve in the form of a stopcock (52). Insufflation port (50) is configured to direct insufflation fluid, such as carbon dioxide, from a fluid source (not shown) distally through working channel (14) and into the patient's abdominal cavity to thereby expand (or "insufflate") the cavity with the fluid. This expansion of the abdominal cavity creates additional space for performing a laparoscopic surgical procedure with improved ease.

As shown in FIGS. 1 and 2, obturator (16) of trocar (10) includes a proximal head (60), an elongate cylindrical shaft (62) extending distally from head (60), and a tapered distal tip (64). Obturator shaft (62) is configured to be received within working channel (14) of cannula assembly (12) such that obturator tip (64) extends through and distally of cannula tip (24). Obturator head (60) includes a domed upper body (66), a base plate (68), and an actuatable latch member (70), which includes a pair of latch arms (72) and a corresponding pair of latch buttons (74). Latch arms (72) are configured to be captured within respective slots (not shown) formed in a top surface of seal housing head (36) to couple obturator (16) with cannula assembly (12). Latch buttons (74) are actuatable to release latch arms (72) from the slots and thereby permit separation of obturator (16) from cannula assembly (12). Obturator (16) further includes a central passage (76) that extends longitudinally through obturator head (60) and obturator shaft (62), and is configured to receive an endoscope (not shown) therein to provide visualization during insertion of trocar (10) through the abdominal wall of a patient. A clamp lever (78) of obturator head (60) is pivotable to selectively fix the endoscope within central passage (76). Central passage (76) and clamp lever (78) are merely optional features and may be omitted from obturator (16) in other versions.

Cannula assembly (12) and obturator (16) may be constructed to be disposed of after a single use with a patient. In other versions, one or more components of trocar (10) may be suitably constructed to withstand sterilization and multiple reuses, for example as described in greater detail below in connection with trocar (110) of FIGS. 4-5.

B. Exemplary Deployment of Trocar Into Patient Abdominal Cavity

FIGS. 3A-3D illustrate an exemplary method of accessing an abdominal cavity (1) of a patient through the patient's abdominal wall (2) with trocar (10) described above. It will be appreciated that abdominal wall (2) includes outward superficial layers and inward deep layers. Superficial layers generally include an outer layer of skin (3) and an inner layer of fat (4); whereas the deeper layers include alternating layers of muscle (5) and fascia (6), which are fibrous and flexible with relatively higher tensile strength than the superficial layers.

Figure 3A:
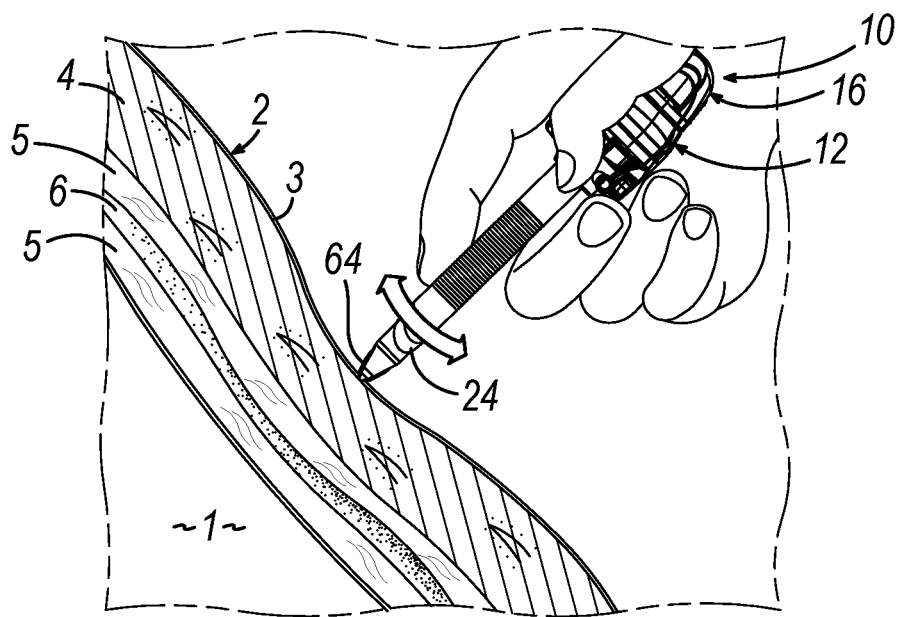
FIG. 3A depicts a side sectional view of the trocar of FIG. 1 being manipulated by a clinician through tissue layers of an abdominal wall.
Figure 3B:
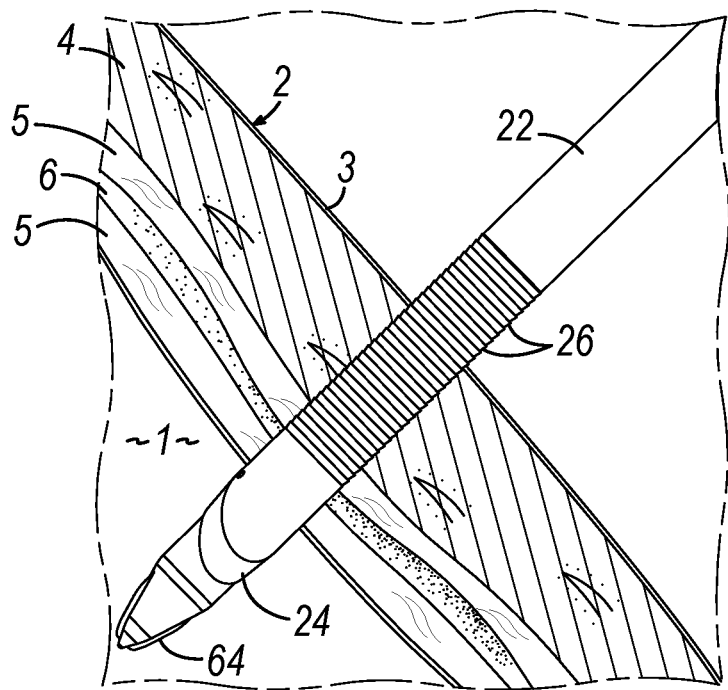
FIG. 3B depicts an enlarged side sectional view of the trocar of FIG. 1, showing a distal end of the trocar received within the abdominal cavity of FIG. 3A.
Figure 3C:
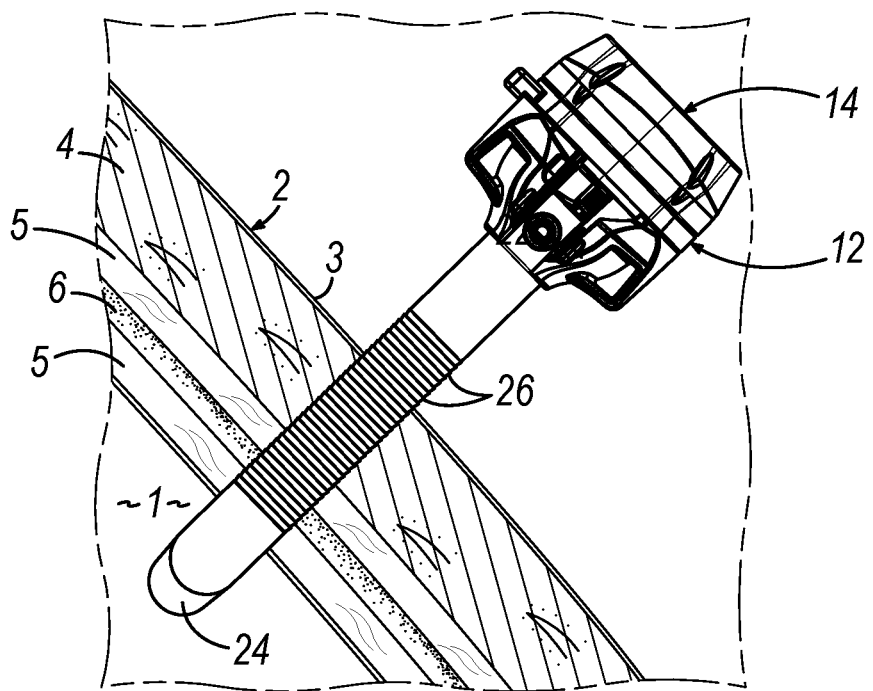
FIG. 3C depicts a side sectional view of the cannula assembly of FIG. 1, showing the cannula assembly remaining positioned within the abdominal wall of FIG. 3A following detachment and removal of the obturator.
Figure 3D:
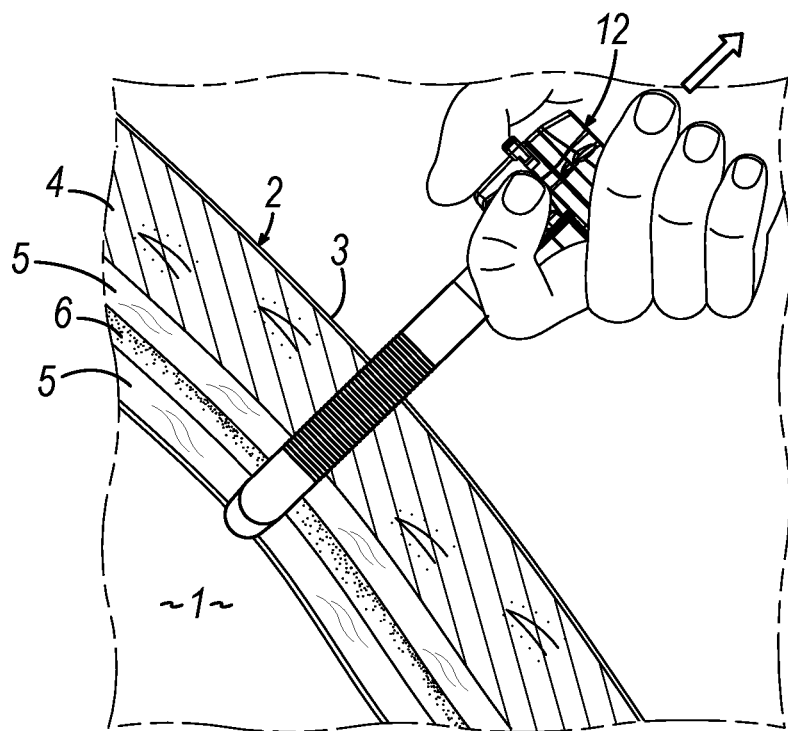
FIG. 3D depicts a side sectional view of the cannula assembly of FIG. 1 being withdrawn proximally from the abdominal wall of FIG. 3A.

As shown in FIG. 3A, with obturator (16) received within cannula assembly (12) and connected to seal housing (30), a clinician manipulates trocar (10) via obturator head (60) and seal housing (30) to urge obturator tip (64) against skin (3) and inward toward abdominal cavity (1) while rotating trocar (10) back and forth. Continued inward urging of trocar (10) further directs obturator tip (64) and cannula tip (24) distally through the layers of fat (4) and fascia (5) and into cavity (1), as shown in FIG. 3B. As discussed above, this step may be facilitated with visualization provided by an endoscope (not shown) mounted within obturator (16). Once cannula (20) has reached a desired depth of insertion into cavity (1), the clinician releases obturator head (60) from seal housing (30) via depression of latch buttons (74), and then withdraws obturator (16) from proximally from cannula assembly (12), as shown in FIG. 3C. This renders working channel (14) of cannula assembly (12) free to receive surgical instruments distally therethrough for performing the laparoscopic surgical procedure. As described above, tissue engagement ribs (26) provided on cannula tube (22) grip the layers of tissue (3, 4, 5) of abdominal wall (2), thus providing cannula assembly (12) with at least a minimum degree of stability relative to abdominal wall (2). Upon completion of the laparoscopic surgical procedure, the clinician grasps seal housing (30) and withdraws cannula assembly (12) proximally from abdominal wall (2), as shown in FIG. 3D.

C. Exemplary Reusable Trocar Having Disposable Seal Assembly

Figure 4:
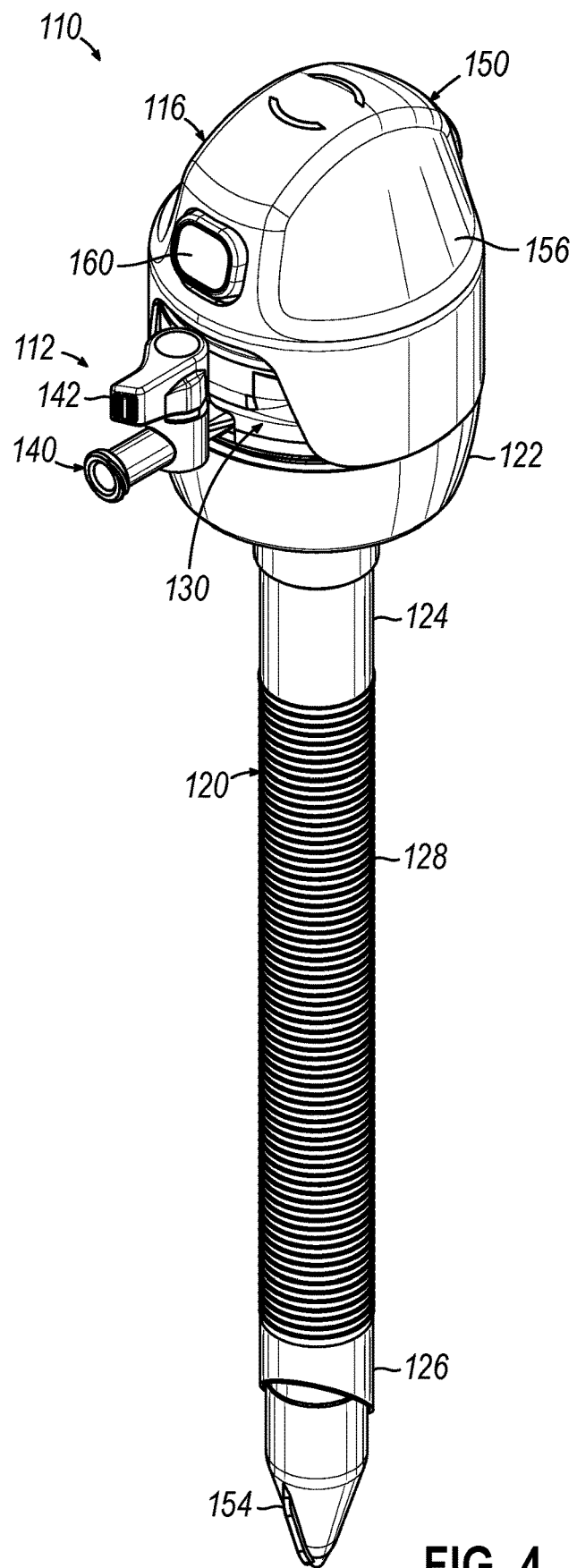
FIG. 4 depicts a perspective view of another exemplary trocar having a cannula assembly and an obturator shown in an assembled state.
Figure 5:
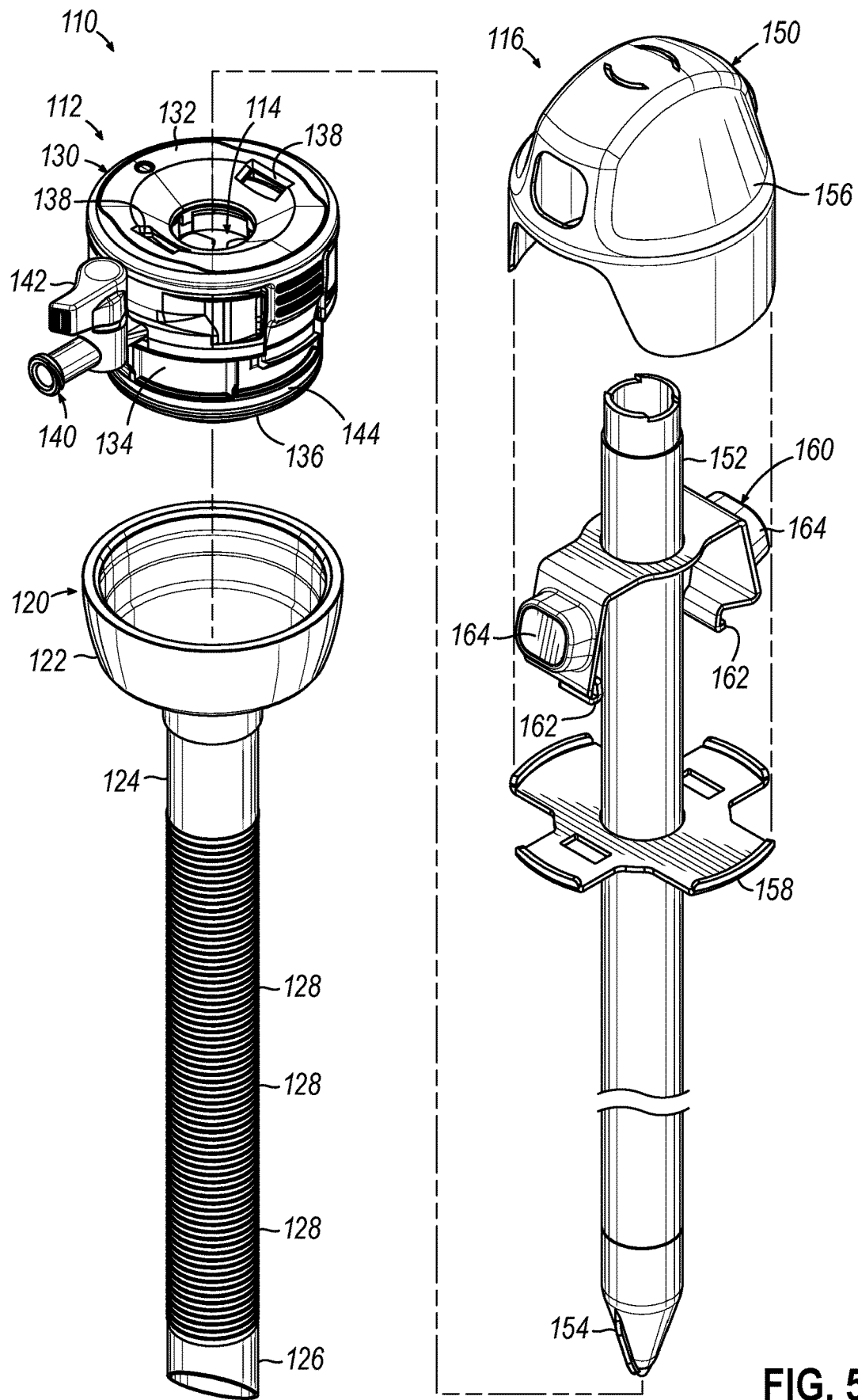
FIG. 5 depicts a perspective view of the cannula assembly and the obturator of FIG. 4 in a disassembled state, showing a reusable cannula and a disposable seal assembly of the cannula assembly separated from one another, and showing the obturator in an exploded state.

In some instances, it may be desirable to configure a trocar such that one or more components thereof may be sterilized and reused for multiple surgical procedures, while one or more other components may be easily and economically disposed of and replaced after each procedure. FIGS. 4-5 show another exemplary trocar (110) that is configured in such a manner, and which is similar in structure and function to trocar (10) described above except as otherwise described below.

Similar to trocar (10), trocar (110) includes a cannula assembly (112) having a working channel (114) and an obturator (116) configured to be inserted into cannula assembly (112) coaxially along working channel (114). Cannula assembly (112) includes a cannula (120) having a bell-shaped hub (122) at a proximal end thereof, and an elongate cylindrical tube (124) extending distally from hub (122) and terminating at an angled cannula tip (126). An outer surface of cannula tube (124) includes a plurality of tissue gripping features in the form of annular ribs (128) arranged axially along a medial portion of cannula tube (124) and which are similar to ribs (26) described above.

Cannula assembly (112) further includes a seal assembly (130). Unlike the seal assembly defined by seal housing (30) of trocar (10), seal assembly (130) is constructed as a modular, replaceable unit configured to releasably mate with proximal hub (122) of cannula (120). As shown best in FIG. 5, seal assembly (130) of the present example generally includes an upper frame member (132), a middle frame member (134), and a lower frame member (136) secured relative to one another in a coaxial arrangement. Though not shown, a proximal (or "outer") seal structure is supported within upper frame member (132), and a distal (or "inner") seal structure is supported within lower frame member (136). Such seal structures may be similar in structure and function to the proximal and distal seal structures of trocar (10) described above. Seal assembly (130) further includes an insufflation port (140) having an adjustable valve in the form of a stopcock (142).

A lower portion of seal assembly (130) distal to insufflation port (140) is configured to seat within proximal hub (122) of cannula (120) such than an annular seal member (144) disposed circumferentially about the lower portion sealingly engages an inner surface of cannula hub (122). In this manner, an interior of seal assembly (130) fluidly communicates with a lumen of cannula (120) to define a working channel (114) of cannula assembly (112) through which insufflation fluid, surgical instruments, and tissue fragments may be directed in the manners generally described above in connection with trocar (10). Seal assembly (130) may be further configured in accordance with one or more teachings of U.S. Pat. Pub. No. 2019/0090905, entitled "Trocar Seal Assemblies," published Mar. 28, 2019, the disclosure of which is incorporated by reference herein; and/or U.S. Pat. Pub. No. 2019/0380742, entitled "Asymmetric Shaft Seal," published Dec. 19, 2019, the disclosure of which is incorporated by reference herein.

As shown best in FIG. 5, obturator (116) of trocar (110) includes a proximal head (150), an elongate cylindrical shaft (152) extending distally from head (150), and a tapered tip (154) at a distal end of shaft (152). Obturator head (150) includes a domed upper body (156), a base plate (158), and an actuatable latch member (160), which includes a pair of downwardly extending latch arms (162) and a corresponding pair of latch buttons (164). Latch arms (162) are configured to be captured within respective slots (138) formed in a top surface of upper frame member (132) of seal assembly (130) to couple obturator (116) with cannula assembly (112). Latch buttons (164) are actuatable to release latch arms (162) from slots (138) and thereby permit separation of obturator (116) from cannula assembly (112).

Cannula (120) and obturator (116) of the present example are suitably constructed of a robust material, such as surgical steel, such that they may be sterilized and reused for multiple surgical procedures. In contrast, as described above, seal assembly (130) is constructed as a disposable unit, intended to be separated from cannula (120) and replaced after each procedure. For instance, seal assembly (130) may be constructed of various polymeric materials, including plastics and rubbers, such that seal assembly (130) may be easily manufactured and sold at a price point that renders seal assembly (130) suitable for disposal after a single use, similar to trocar (10) described above.

II. Exemplary Universal Size Multi-Walled Elastomer Depth Limiters

In some instances, a clinician may desire to limit the depth to which a single-use or reusable trocar (10, 110) may travel into abdominal wall (2) (e.g., after insertion of trocar (10, 110) to a desired position). Limiting the depth to which trocar (10, 110) may travel into abdominal wall (2) may assist in preventing distal tip (64, 154) of obturator (16, 116) and/or cannula tip (24, 126) of cannula assembly (12, 112) from inadvertently entering deeper than desired into abdominal cavity (1). Preventing over insertion of trocar (10, 110) may reduce undesirable contact of distal tip (64, 154) and/or cannula tip (24, 126) with anatomical structures contained within abdominal cavity (1). Preventing over insertion of trocar (10, 110) may also avoid inadvertently reducing the available surgical working space within abdominal cavity (1).

Alternatively or in addition to limiting the depth to which single-use or reusable trocar (10, 110) may travel into abdominal wall (2), the clinician may desire to stabilize trocar (10, 110) relative to abdominal wall (2) (e.g., after insertion of trocar (10, 110) to a desired position in abdominal cavity (1)). The clinician may stabilize trocar (10, 110) relative to abdominal wall (2) by avoiding under insertion of trocar (10, 110). Stabilizing trocar (10, 110) relative to abdominal wall (2) after insertion into abdominal wall (2) may assist in preventing trocar (10, 110) from inadvertently pivoting about the insertion point in abdominal wall (2) after the clinician releases trocar (10, 110). Stabilizing trocar (10, 110) maintains cannula tip (24, 126), and thus, the entry point of surgical instruments into abdominal cavity (1) in a desired position and/or orientation relative to abdominal cavity (1) such that surgical instruments may be easily directed distally through trocar (10, 110) at a selected working angle that is convenient for the clinician.

A. Exemplary Universal Size Multi-Walled Elastomer Depth Limiter

Figure 6:
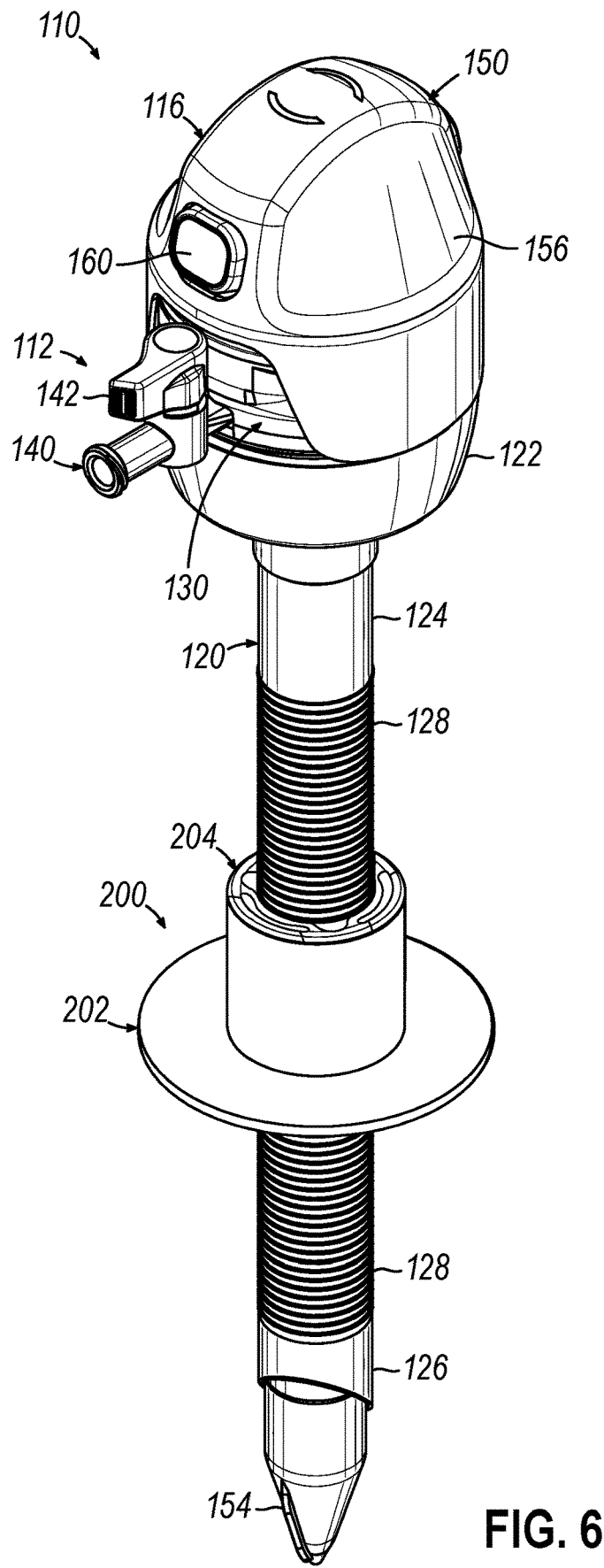
FIG. 6 depicts a perspective view of the trocar of FIG. 4, showing an exemplary depth limiter selectively coupled to the cannula tube of the cannula assembly.

FIG. 6 shows a first exemplary depth limiter (200) selectively coupled to cannula tube (124) of second trocar (110). As described in greater detail below, depth limiter (200) may selectively limit the depth to which trocar (110) may travel distally into abdominal wall (2).

Figure 7:
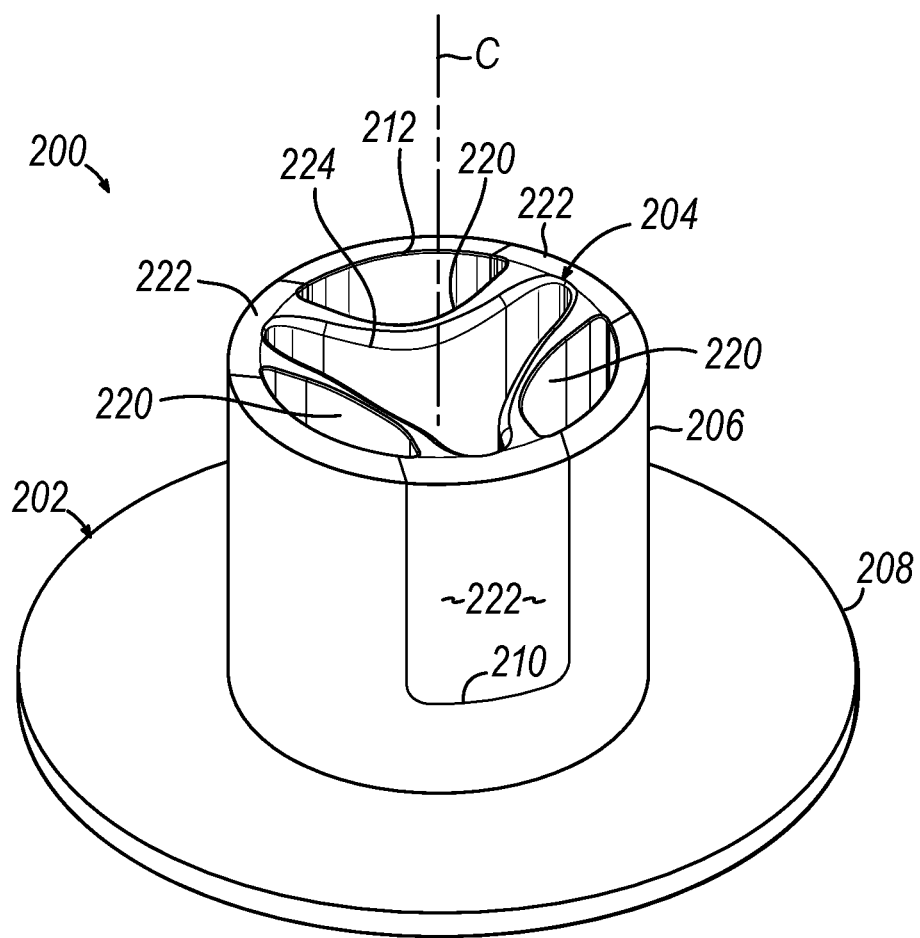
FIG. 7 depicts a perspective view of the depth limiter of FIG. 6.
Figure 8A:
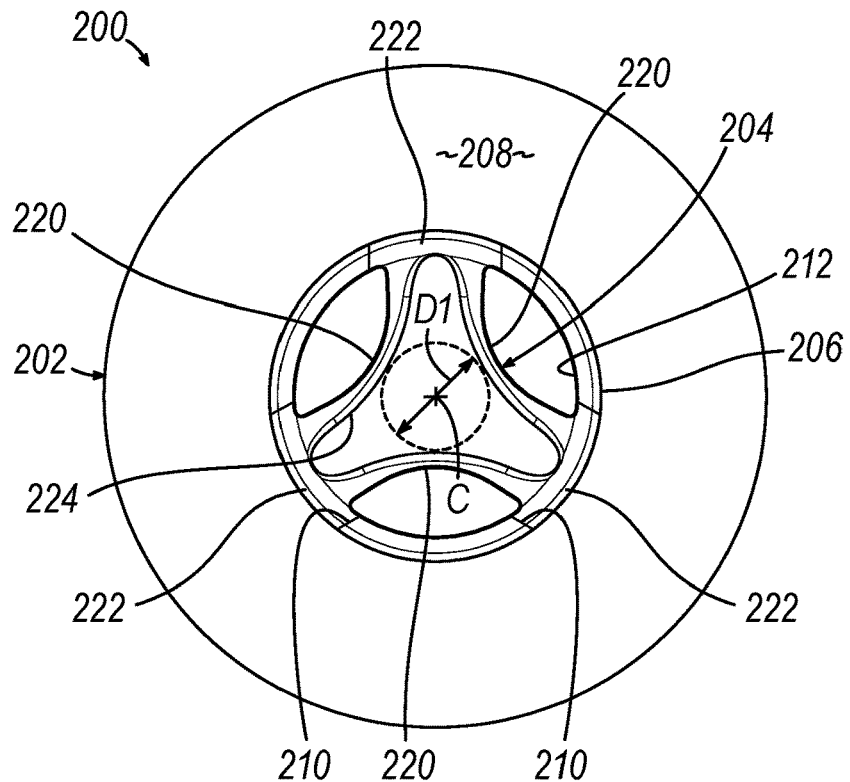
FIG. 8A depicts a top elevational view of the depth limiter of FIG. 6, showing the lobes of the depth limiter in a relaxed configuration.
Figure 8B:
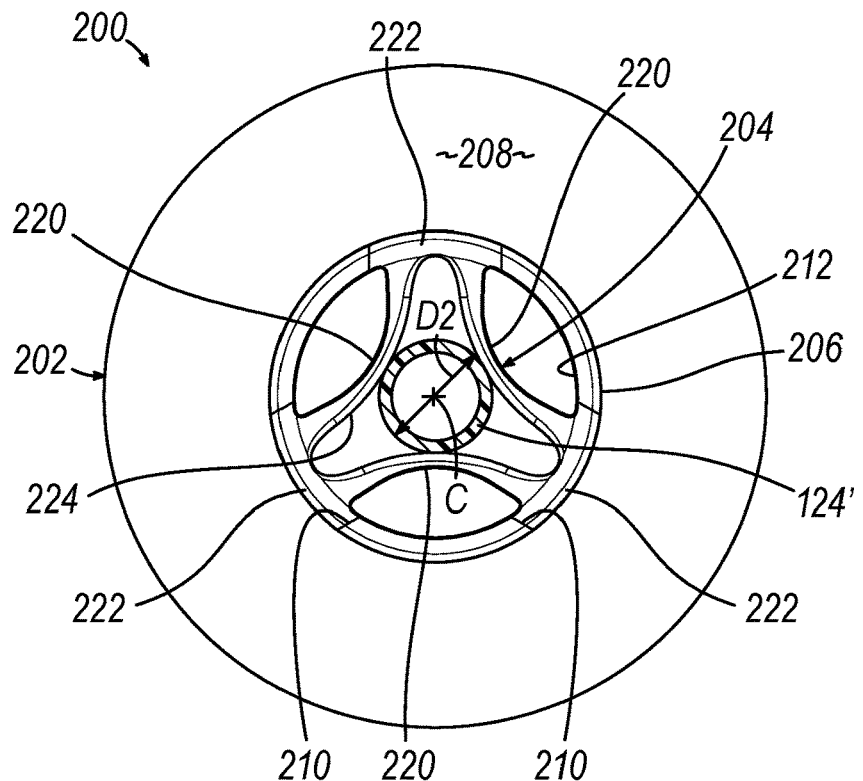
FIG. 8B depicts a top elevational view similar to FIG. 8A, showing the depth limiter of FIG. 6 positioned about a cannula tube having a smaller cross dimension than that of the trocar of FIG. 4 such that the lobes of the depth limiter are urged radially outwardly by the cannula tube to a first flexed configuration to selectively couple the depth limiter to the cannula tube.
Figure 8C:
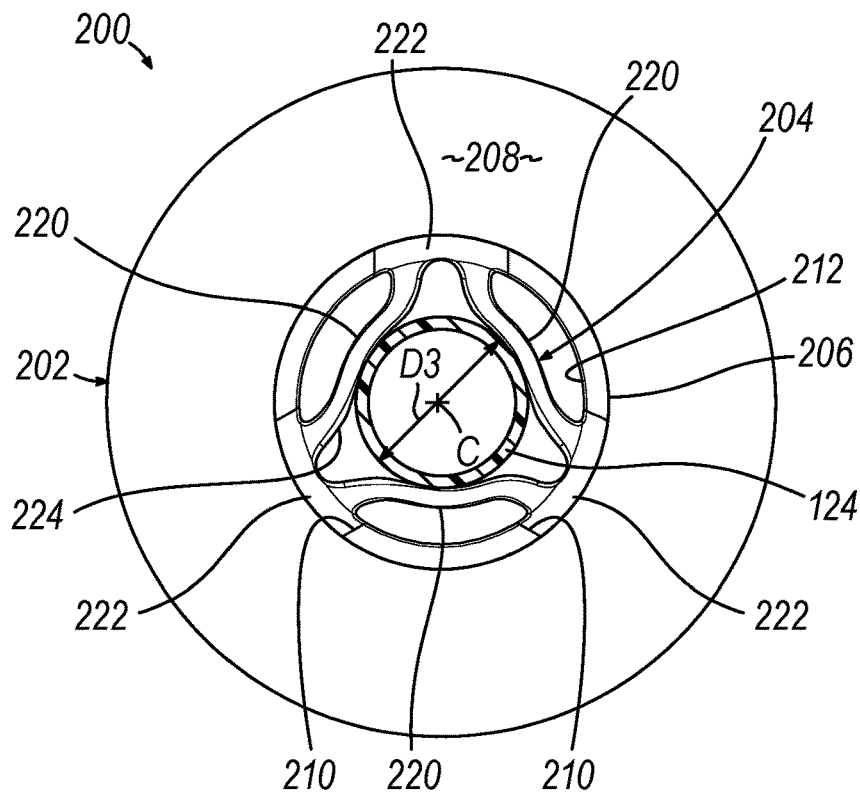
FIG. 8C depicts a top elevational view similar to FIG. 8B, showing the depth limiter of FIG. 6 positioned about the cannula tube of the trocar of FIG. 4 such that the lobes of the depth limiter are urged radially outwardly by the cannula tube to a second flexed configuration to selectively couple the depth limiter to the cannula tube.

As best shown in FIGS. 7-8C, depth limiter (200) includes a relatively rigid outer frame portion (202) housing a relatively flexible inner gripping portion (204) such that inner gripping portion (204) is flexible relative to outer frame portion (202) between at least one relaxed configuration (e.g., FIG. 8A) and at least one flexed configuration (e.g., FIGS. 8B and 8C). For instance, outer frame portion (202) may be constructed of a relatively rigid polymeric material, such as a plastic material (e.g., polycarbonate), and inner gripping portion (204) may be constructed of a relatively flexible elastomeric material, such as a rubber material. In one example, outer frame portion (202) and inner gripping portion (204) are integrally formed together as a unitary piece. For example, depth limiter (200) may be constructed via a two-shot molding process (also known as "overmolding") such that outer frame portion (202) and inner gripping portion (204) are each injection molded, with one being injection molded over the other. In another example, outer frame portion (202) and inner gripping portion (204) are separately formed from each other as distinct pieces, and inner gripping portion (204) is assembled onto outer frame portion (202) after formation thereof. Such constructions may allow depth limiter (200) to be considered a disposable unit, intended to be separated from cannula (120) and replaced after each procedure. For instance, such a construction may allow depth limiter (200) to be easily manufactured and sold at a price point that renders depth limiter (200) suitable for disposal after a single use, similar to trocar (10) and seal assembly (130) described above. In other versions, one or more portions of depth limiter (200) may be formed of surgical steel or other material suitable to render depth limiter sterilizable and reusable for multiple surgical procedures.

In the example shown, depth limiter (200) has a generally hollow, top hat-shaped profile. To this end, outer frame portion (202) includes a proximal cylindrical hub (206) and a distal flat annular flange (208) extending radially outwardly therefrom. Cylindrical hub (206) includes a plurality of proximally-facing recesses (210) circumferentially spaced thereabout uniformly, and defines a generally cylindrical bore (212) which extends longitudinally along a central axis (C) of depth limiter (200). In the example shown, cylindrical hub (206) includes three generally elongate, rectangular recesses (210). As described in greater detail below, recesses (210) and bore (212) are configured to collectively receive inner gripping portion (204).

In this regard, inner gripping portion (204) includes a plurality of flexible walls or lobes (220) interconnected at or near radially outer terminal ends thereof via respective vertices or joints (222). In the example shown, inner gripping portion (204) includes three lobes (220) interconnected at three respective generally elongate, rectangular joints (222) such that inner gripping portion (204) has a generally triangular profile. While outer frame portion (202) is shown having three recesses (210) and inner gripping portion (204) is shown having three corresponding lobes (220) and joints (222), other versions of depth limiter (200) could be provided with various other quantities and arrangements of these features.

In the example shown, each lobe (220) is resiliently biased radially inwardly along a length thereof relative to central axis (C) toward a relaxed configuration, as shown in FIG. 8A. To this end, the illustrated lobes (220) are each bent radially inwardly along an arcuate or curved path, at least when lobes (220) are in the relaxed configuration. Joints (222) are securely received within corresponding recesses (210) of cylindrical hub (206) to thereby couple inner gripping portion (204) to outer frame portion (202). Lobes (220) are flexibly received within bore (212) of cylindrical hub (206) such that lobes (220) are permitted to flex radially outwardly from the relaxed configuration toward at least one flexed configuration to thereby grip an outer surface of cannula tube (124) of trocar (110), as shown in FIGS. 8B and 8C. For instance, an inner surface of bore (212) may be spaced apart from lobes (220), at least when lobes (220) are in the relaxed configuration. In this manner, lobes (220) collectively define an expandable generally triangular bore (224) extending longitudinally along central axis (C) of depth limiter (200), and having an unexpanded configuration when lobes (220) are in the relaxed configuration and having at least one expanded configuration when lobes (220) are in the at least one flexed configuration.

More particularly, and as shown in FIG. 8A, when lobes (220) are in the relaxed configuration, lobes (220) may collectively form a first effective cross dimension (D1) that extends diametrically between radially inward-most portions or apexes of lobes (220) through central axis (C) and is smaller than a cross dimension of cannula tube (124) of trocar (110). As shown in FIG. 8B, when lobes (220) are in a first flexed configuration, lobes (220) may collectively form a second effective cross dimension (D2) that extends diametrically between radially inward-most portions or apexes of lobes (220) through central axis (C) and is substantially equal to the cross dimension of a cannula tube (124') (which is smaller than a cross dimension of cannula tube (124)) to selectively restrict axial movement of depth limiter (200) relative to cannula tube (124'). In this regard, a frictional interference condition may be generated between cannula tube (124') and lobes (220). In one example, second effective cross dimension (D2) may be equal to approximately 5 mm. And as shown in FIG. 8C, when lobes (220) are in a second flexed configuration, lobes (220) may collectively define a third effective cross dimension (D3) that extends diametrically between radially inward-most portions or apexes of lobes (220) through central axis (C) and is substantially equal to a cross dimension of cannula tube (124) to selectively restrict axial movement of depth limiter (200) relative to cannula tube (124). In this regard, a frictional interference condition may be generated between cannula tube (124) and lobes (220). In one example, third effective cross dimension (D3) may be equal to approximately 12 mm.

The illustrated lobes (220) are configured to directly grip an outer surface of cannula tube (124, 124'), such as ribs (128), when urged to the respective flexed configuration by cannula tube (124, 124'), and thereby generate the frictional interference condition to restrict axial movement of depth limiter (200) relative to cannula tube (124, 124') via the resilience of lobes (220). In some examples, each lobe (220) is configured to extend across and grip a plurality of ribs (128). It will be appreciated that lobes (220) may include one or more tube gripping features such as textured radially inner surfaces or radially inwardly extending ridges (not shown) configured to grip an outer surface of cannula tube (124, 124'), such as ribs (128), and thereby assist in restricting axial movement of depth limiter (200) relative to cannula tube (124, 124').

Thus, lobes (220) may be configured to accommodate and frictionally engage cannula tubes (124, 124') having a variety of cross dimensions including cannula tubes (124, 124') having cross dimensions equal to between approximately 5 mm and approximately 12 mm, for example. It will be appreciated that such frictional engagement between lobes (220) and cannula tube (124, 124') may be overcome by a threshold pushing (e.g., distally directed) or pulling (e.g., proximally directed) force applied by a user's hand to depth limiter (200) sufficient to frictionally disengage lobes (220) from cannula tube (124, 124') and allow for axial movement of depth limiter (200) relative to cannula tube (124, 124'), such as by sliding lobes (220) along cannula tube (124, 124').

During operation, and with continuing reference to FIGS. 8A-8C, depth limiter (200) may be initially positioned about cannula tube (124, 124') of trocar (110) such that cannula tube (124, 124') urges lobes (220) radially outwardly from the relaxed configuration shown in FIG. 8A to the respective flexed configuration shown in FIG. 8B or 8C to allow cannula tube (124, 124') to be received within expandable bore (224) prior to deployment of trocar (110) into the patient's abdominal cavity (1). In one example, central axis (C) of depth limiter (200) may coincide with a central axis (not shown) of trocar (110).

During deployment of trocar (110) into abdominal cavity (1), lobes (220) may remain in the flexed configuration to thereby restrict axial movement of depth limiter (200) relative to cannula tube (124, 124') of trocar (110). For example, the clinician may desire to position depth limiter (200) at a predetermined axial location along cannula tube (124, 124') corresponding to a desired depth of insertion of cannula (120) within cavity (1). Thus, the clinician may manipulate depth limiter (200) to apply a threshold pushing or pulling force thereto sufficient to overcome the frictional engagement between lobes (220) and cannula tube (124, 124') to effectively and ergonomically move depth limiter (200) axially along cannula tube (124, 124') by sliding lobes (220) along cannula tube (124, 124') to the predetermined axial location. Once depth limiter (200) is at the predetermined axial location, the clinician may release depth limiter (200), thereby allowing the frictional engagement between lobes (220) and cannula tube (124, 124') to maintain depth limiter (200) at the predetermined axial location.

With depth limiter (200) positioned about cannula tube (124, 124'), the clinician may deploy trocar (110) into the patient's abdominal cavity (1) as described above with respect to FIGS. 3A and 3B to position cannula (120) at a desired depth of insertion in cavity (1). Contact between distal flange (208) of depth limiter (200) and abdominal wall (2) may provide a visual and/or tactile indication to the clinician that cannula (120) has reached the desired depth of insertion in cavity (1). In this manner, depth limiter (200) may assist in preventing distal tip (154) of obturator (116) and/or cannula tip (126) of cannula assembly (112) from inadvertently entering deeper than desired into abdominal cavity (1) during deployment.

In some cases, it may be desirable to adjust the axial location of depth limiter (200) along cannula tube (124, 124') after depth limiter (200) has already been coupled to cannula tube (124, 124'). Thus, the clinician may again manipulate depth limiter (200) to apply a threshold pushing or pulling force thereto sufficient to overcome the frictional engagement between lobes (220) and cannula tube (124, 124') to effectively and ergonomically move depth limiter (200) axially along cannula tube (124, 124') by sliding lobes (220) along cannula tube (124, 124') to a new axial location. Once depth limiter (200) is at the new axial location, the clinician may release depth limiter (200), thereby allowing lobes (220) and cannula tube (124, 124') to frictionally reengage to maintain depth limiter (200) at the new axial location. Thus, the clinician may adjust the axial location of depth limiter (200) along cannula tube (124, 124'), and may subsequently re-secure depth limiter (200) to cannula tube (124, 124') by simply releasing depth limiter (200).

Depth limiter (200) may remain securely coupled to cannula tube (124, 124') during performance of the laparoscopic surgical procedure with distal flange (208) of depth limiter (200) resting against abdominal wall (2). In this manner, depth limiter (200) may assist in preventing cannula tip (126) of cannula assembly (112) from inadvertently entering deeper than desired into abdominal cavity (1) during performance of the laparoscopic surgical procedure, and may also assist in stabilizing cannula tube (124, 124') relative to abdominal wall (2).

Upon completion of the laparoscopic surgical procedure, depth limiter (200) may be withdrawn proximally from abdominal wall (2) together with cannula assembly (112). Depth limiter (200) may be removed from cannula tube (124, 124') by overcoming the frictional engagement between lobes (220) and cannula tube (124, 124') as described above. In one example, depth limiter (200) may be simply disposed of after completion of a single laparoscopic surgical procedure.

Figure 9:
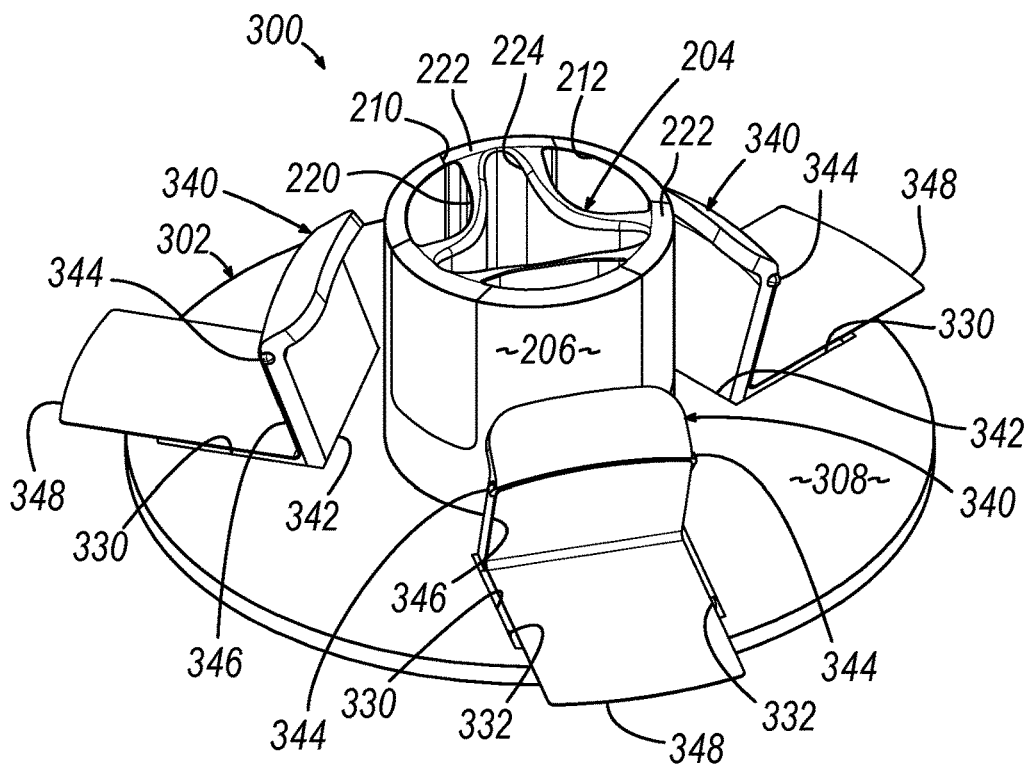
FIG. 9 depicts a perspective view of another exemplary depth limiter having a plurality of stability tabs.

B. Exemplary Universal Size Multi-Walled Elastomer Depth Limiter with Stability Tabs In some instances, it may be desirable to provide a cannula depth limiter with additional stabilizing features to more securely stabilize a trocar relative to the abdominal wall (2) of a patient. FIG. 9 shows a second exemplary depth limiter (300) that includes such features. Similar to depth limiter (200), depth limiter (300) may selectively limit the depth to which trocar (110) may travel distally into abdominal wall (2). Depth limiter (300) is substantially similar to depth limiter (200) and includes various similar features. Thus, only different features are described below.

Depth limiter (300) of the present version includes outer frame portion (302) including proximal cylindrical hub (206) and a distal flat annular flange (308) extending radially outwardly therefrom. Flange (308) is generally similar to flange (208), except that flange (308) includes a plurality of apertures (330) circumferentially spaced thereabout and further includes pairs of inwardly-facing protrusions (332) positioned on opposing sides of each aperture (330). Outer frame portion (302) further includes a plurality of stability tabs (340) pivotably coupled to flange (308) by respective hinges (342) adjacent corresponding apertures (330) such that each stability tab (340) is pivotable relative to flange (308) between a respective deployed configuration wherein stability tab (340) is received within aperture (330) and a respective retracted configuration wherein stability tab (340) is pivoted proximally away from aperture (330) about hinge (342). The illustrated hinges (342) each include a thinned portion of the same material as flange (308) and stability tabs (340) such that stability tabs (340) are permitted to bend thereabout relative to flange (308), such that each may be considered a "living" hinge.

Each stability tab (340) includes a pair of outwardly-facing protrusions (344) positioned on opposing sides thereof and a distal adhesive surface (346). Protrusions (344) are configured to selectively engage peripheral edges of the corresponding aperture (330), such as protrusions (332), when stability tab (340) is in the deployed configuration, to generate a frictional interference condition therewith to assist in maintaining stability tab (340) in the deployed configuration.

Distal adhesive surfaces (346) may each include a glue or other adhesive applied to a distal surface of the respective stability tab (340). Each distal adhesive surface (346) is configured to selectively adhere the respective stability tab (340) to abdominal wall (2) when distal flange (308) is resting against abdominal wall (2) and the respective stability tab (340) is in the deployed configuration. In this manner, stability tabs (340) may assist in stabilizing depth limiter (300) together with trocar (10, 110) relative to abdominal wall (2). In the example shown, each distal adhesive surface (346) is selectively covered by a corresponding removable adhesive mask (348) for protecting distal adhesive surfaces (346) from undesirably adhering to surfaces that distal adhesive surfaces (346) may otherwise inadvertently come into contact with.

Figure 10A:
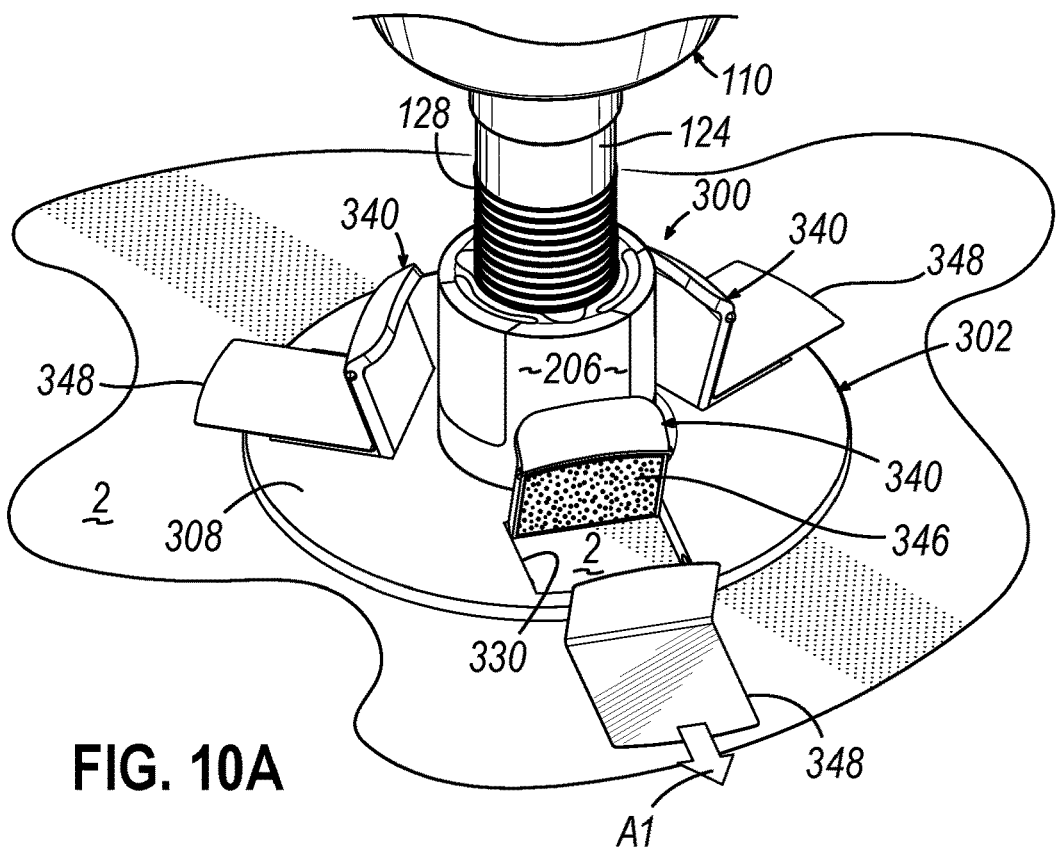
FIG. 10A depicts a perspective view of the depth limiter of FIG. 9 selectively coupled to the cannula tube of the trocar of FIG. 4 and resting against the abdominal wall of FIG. 3A during manipulating of the trocar by a clinician through tissue layers of the abdominal wall.
Figure 10B:
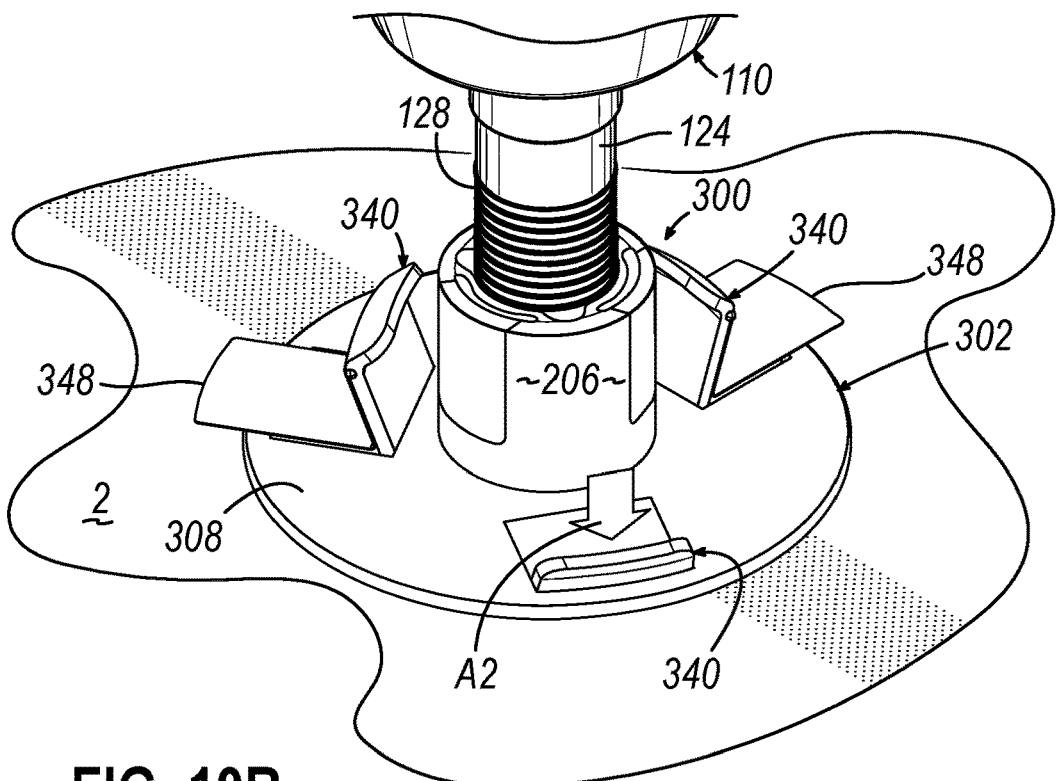
FIG. 10B depicts a perspective view similar to FIG. 10A, showing the depth limiter of FIG. 9 being selectively attached to the abdominal wall via the stability tabs.

During operation, and with reference to FIGS. 10A-10B, depth limiter (300) may be initially positioned about cannula tube (124, 124') of trocar (110) as described above with respect to FIGS. 8A-8C prior to deployment of trocar (110) into the patient's abdominal cavity (1), and the clinician may then deploy trocar (110) into the patient's abdominal cavity (1) as described above with respect to FIGS. 3A and 3B. Once distal flange (308) contacts abdominal wall (2) and rests thereagainst, the clinician may remove adhesive masks (348) from distal adhesive surfaces (346), as indicated by first arrow (A1) in FIG. 10A, and pivot each stability tab (340) relative to flange (308) about the respective hinge (342) from the respective retracted configuration to the respective deployed configuration, as indicated by second arrow (A2) in FIG. 10B, such that each stability tab (340) is received within the respective aperture (330) to allow the respective distal adhesive surface (346) to contact abdominal wall (2). Distal adhesive surfaces (346) may thereby adhere stability tabs (340) to abdominal wall (2).

C. Third Exemplary Depth Limiter

Figure 11:
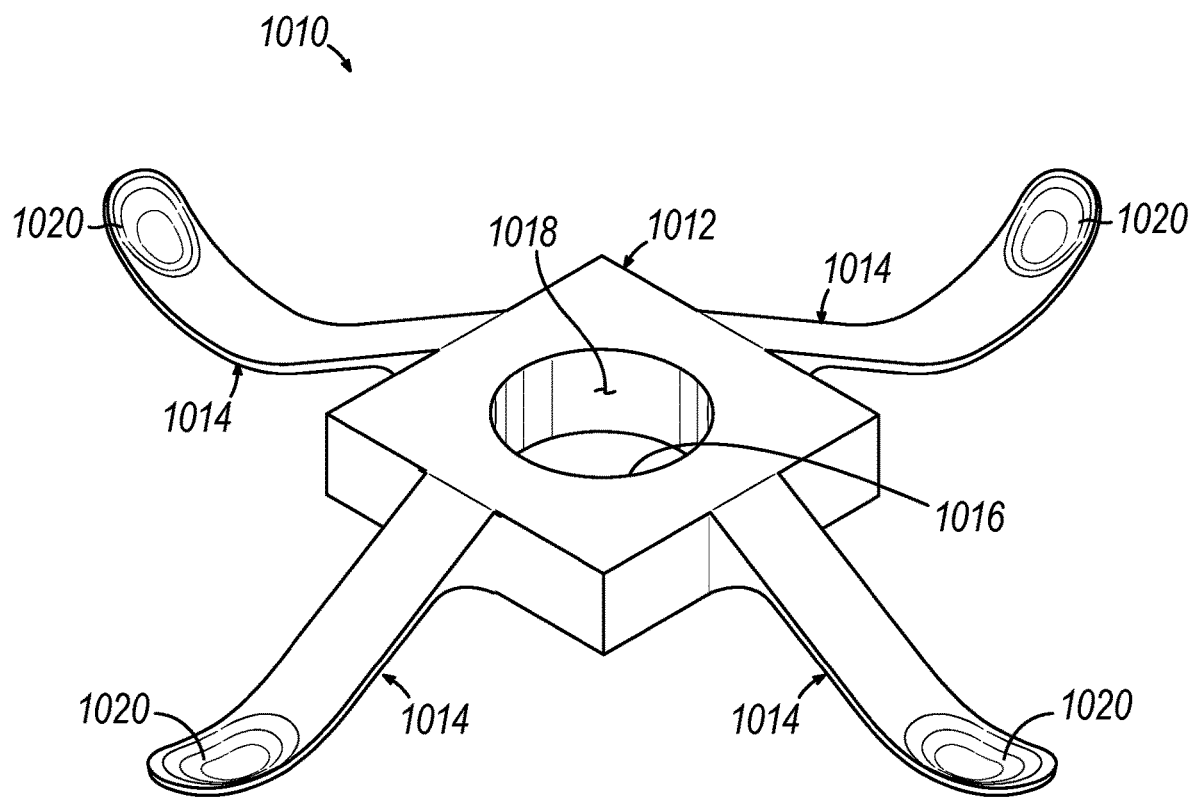
FIG. 11 depicts a perspective view of another exemplary depth limiter that includes four legs.

FIG. 11 shows a perspective view of a third exemplary depth limiter (1010).

Depth limiter (1010) includes a hub (1012) and a plurality of legs (1014). Depth limiter (1010) may be used in combination with depth limiters (200, 300) described above. While hub (1012) is shown as being generally square shaped, other shapes of hub (1012) are also envisioned. As shown, hub (1012) includes an aperture (1016) extending completely therethrough. Aperture (1016) may include a gripping surface (1018). Gripping surface (1018) may extend parallel to a longitudinal axis defined by cannula tube (22) of cannula (20). While FIGS. 11-12B describe depth limiter (1010) with reference to cannula tube (22) of trocar (10) of FIG. 1, other cannula tubes (e.g., cannula tube (124)) may also be used. Gripping surface (1018) may be smooth or non-smooth. As shown in FIG. 11, gripping surface (1018) includes a smooth surface that may frictionally engage a portion of cannula (20), such as ribs (26). Alternatively, gripping surface (1018) may include a non-smooth surface may include one or more features to lockingly engage cannula tube (22). In other words, depth limiter (1010) may be secured to cannula (20) with mating threads (like a nut) or secured to a scalloped cannula with an appropriate amount of interference fit. Such threads of depth limiter (1010) may be helical or non-helical (e.g., scallops). For example, gripping surface (1018) may include at least one tooth configured to lockingly engage with at least one of rib (26) of cannula (20).

Legs (1014) may have a generally constant cross-sectional area moving radially away from hub (1012); however, legs (1014) may have a non-uniform cross-section. For example, one or more ends of legs (1014) may include cupped potions (1020) to distribute the downward force. As shown, legs (1014) are separated by approximately 90 degrees. More or fewer legs (1014) are also envisioned.

Depth limiter (1010) may provide additional stability to the trocar (10) for anti-tip resistance. Depth limiter (1010) may be configured to restrict sudden tilting using legs (1014), thereby stabilizing cannula (20). Depth limiter (1010) is configured to prevent accidental over-insertion into body, while also restricting the displacement and/or velocity of off-axis tilting of trocar (10) to stabilize trocar (10). This stabilization may be achieved using mechanical spring effects of each leg (1014). Legs (1014) may have a reduced mass allowing legs (1014) to flex outwardly, causing a variable amount of spring-resistance in each direction trocar (10) attempts to tilt. For example, legs (1014) may have reduced mass portions (e.g., living hinge portions), and/or may rely on inherent spring force of legs (1014). Legs (1014) may contact the patient's body wall to prevent or at least decelerate tip over of cannula (20).

Figure 12A:
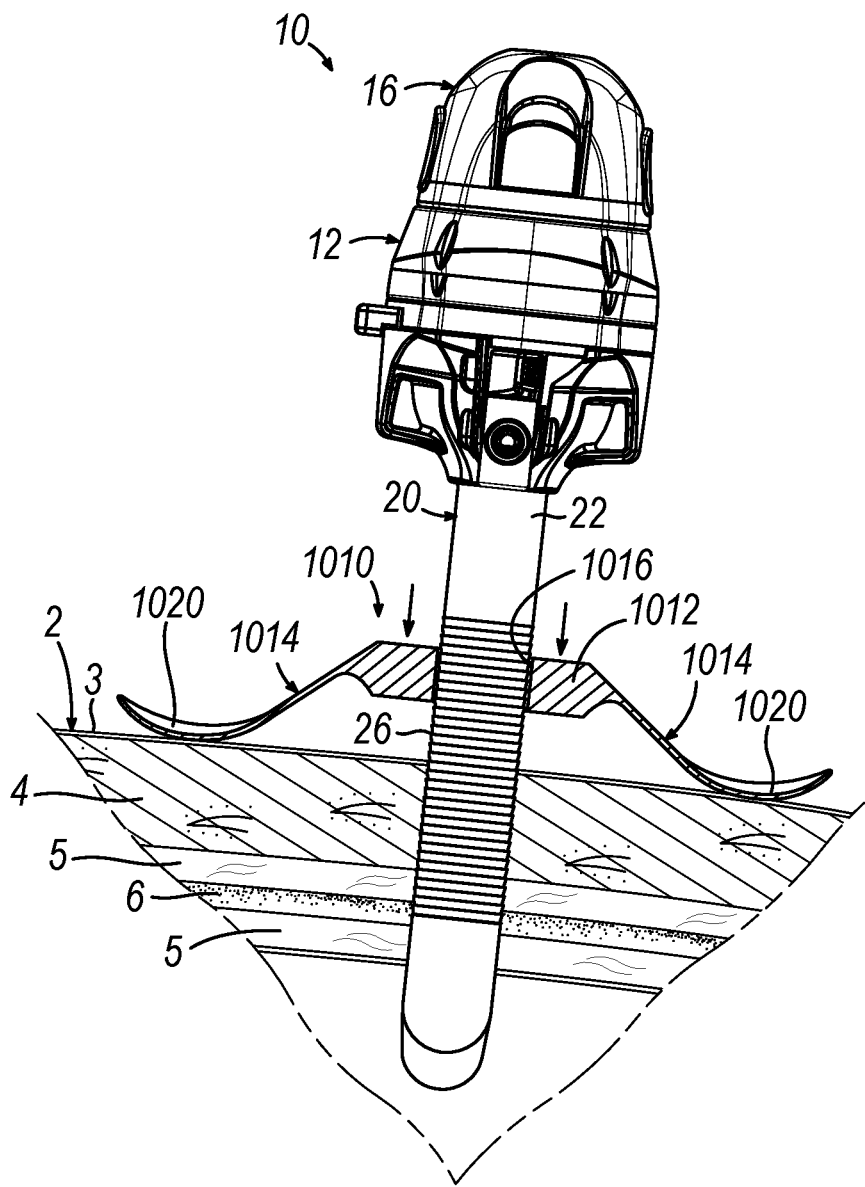
FIG. 12A depicts a partial side sectional view of the depth limiter of FIG. 11 coupled with the cannula tube of the cannula assembly of the trocar of FIG. 1, where the legs of the depth limiter are in a non-deployed configuration when the distal end of the trocar received within the abdominal cavity.
Figure 12B:
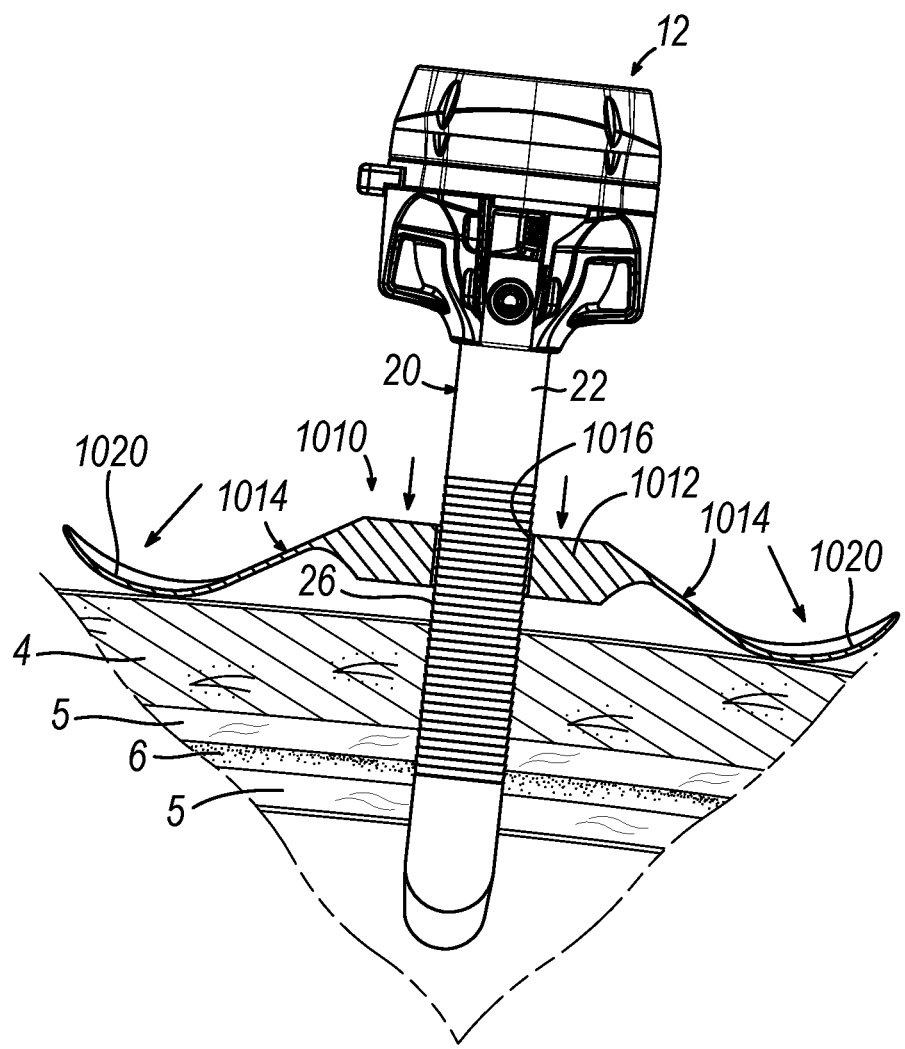
FIG. 12B depicts a partial side sectional view of the depth limiter of FIG. 11 coupled with the cannula tube of the cannula assembly of FIG. 1 following detachment and removal of the obturator, where the legs of the depth limiter are in a deployed configuration with a distal end of the cannula tube received within the abdominal cavity.

FIGS. 12A-12B show depth limiter (1010); however, the teachings of FIGS. 12A-12B may also apply to depth limiters (1110, 1210) described in detail below. FIG. 12A shows a partial side sectional view of depth limiter (1010) of FIG. 11 coupled with cannula tube (22) of cannula assembly (12) of trocar (10) of FIG. 1, where legs (1014) of depth limiter (1010) are in a non-deployed configuration when distal end of trocar (10) received within abdominal cavity (1). In the non-deployed configuration (e.g., the resting configuration) of FIG. 12A, legs (1014) may be curved downwardly. As depth limiter (1010) is pushed against abdominal wall (2), legs (1014) bend flatter and provide reaction spring-forces against abdominal wall (2) and cannula (20). The degree at which legs (1014) bend flatter may be controlled by the user. For example, additional force (e.g., downward hand pressure by the user) may cause legs (1014) to bend flatter until depth limiter (1010) is disposed adjacent to abdominal wall (2). As the flatness of legs (1014) increases, the amount of reactive forces on cannula (20) may also increase, which increases the locking force. For example, when the user has depressed depth limiter (1010) to a partially (but not fully) deployed configuration, legs (1014) may have some degree of deployment. Additionally, if the user then applies an off-axis loading, one or more of legs (1014) may depress further than the other legs (1014), but upon removal of the off-axis load, legs (1014) may be equalized and return in a controlled manner to a centered home position.

FIG. 12B shows a partial side sectional view of depth limiter (1010) of FIG. 11 coupled with cannula tube (22) of cannula assembly (12) of FIG. 1 following detachment and removal of obturator (16), where legs (1014) of depth limiter (1010) are in a deployed configuration with a distal end of cannula tube (22) received within abdominal cavity (1). In the deployed configuration, legs (1014) may reduce the amount of rotational displacement/tilt that trocar (10)) may achieve, and may also reduce the velocity that trocar (10) may achieve that tilt (i.e., preventing sudden accidental moves within the body). To completely undeploy depth limiter (1010) from cannula tube (22), the user may retract cannula (20) out of abdominal wall (2) to sufficiently reduce the compressive/clamping forces of depth limiter (1010) on the abdominal wall (2), such that the user may pull the depth limiter (1010) back using their hand. Depth limiter (1010) may be disposable or re-usable.

D. Fourth Exemplary Depth Limiter

Figure 13:
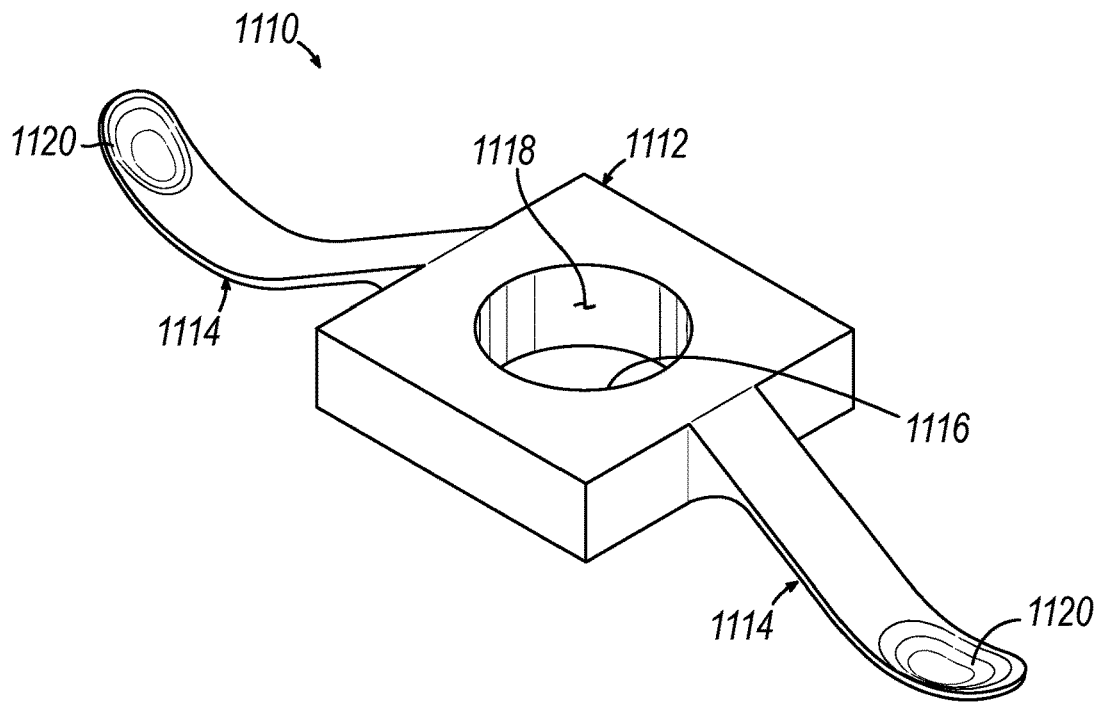
FIG. 13 depicts a perspective view of another exemplary depth limiter that includes two legs.

FIG. 13 shows a fourth exemplary depth limiter (1110) that is similar to depth limiter (1010). Depth limiter (1110) includes a hub (1112) similar to hub (1012), legs (1114) similar to legs (1014), an aperture (1116) similar to aperture (1016), a gripping surface (1118) of aperture (1116) similar to gripping surface (1018). Legs (1114) may include cupped portions (1120) similar to cupped portions (1020). Unlike depth limiter (1010) that is shown as including four legs (1014), depth limiter (1110) includes two legs (1114). For example, legs (1114) may be separated by approximately 180 degrees. Legs (1114) flex similar to legs (1014) shown above with reference to FIGS. 12A-12B.

E. Fifth Exemplary Depth Limiter

Figure 14:
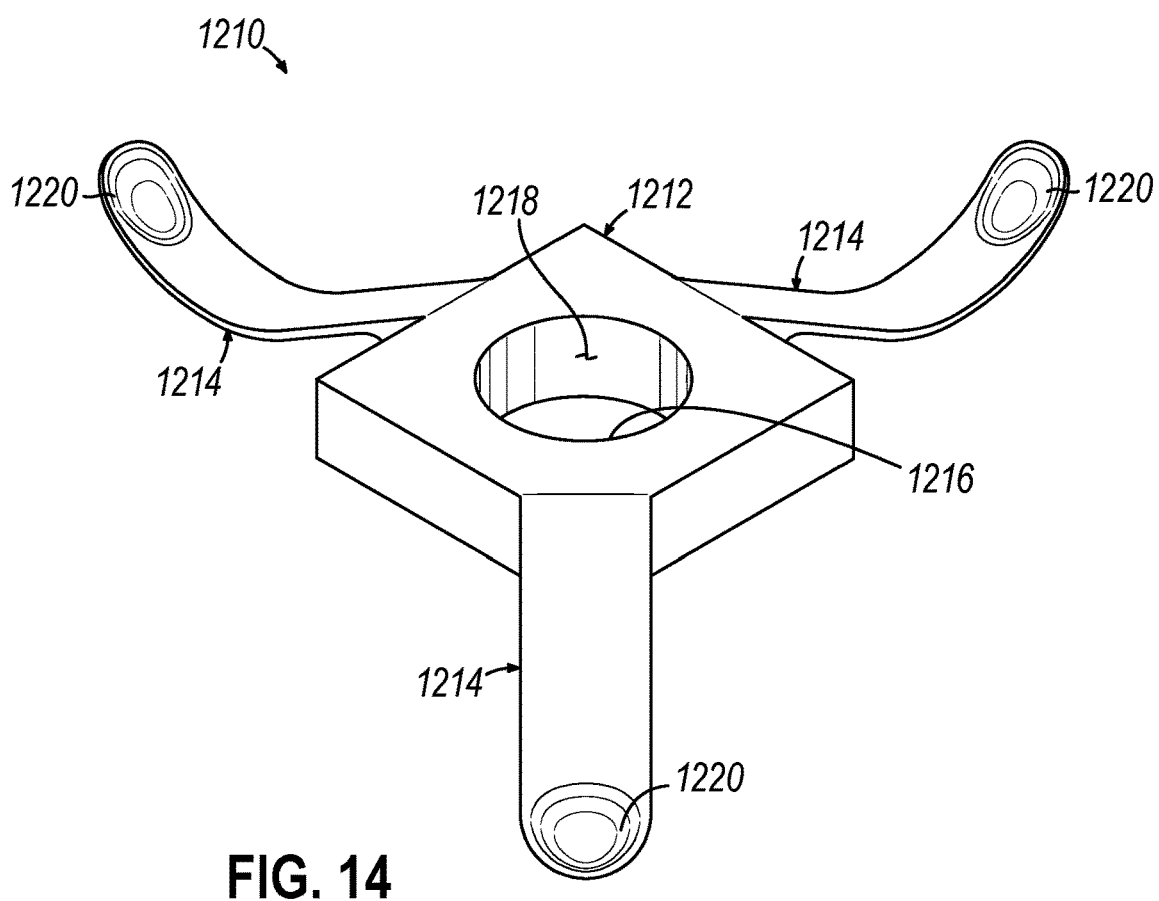
FIG. 14 depicts a perspective view of another exemplary depth limiter that includes three legs.

FIG. 14 shows a fifth exemplary depth limiter (1210) that is similar to depth limiters (1010, 1110). Depth limiter (1210) includes a hub (1212) similar to hub (1012), legs (1214) similar to legs (1014), an aperture (1216) similar to aperture (1016), a gripping surface (1218) of aperture (1216) similar to gripping surface (1018). Legs (1114) may include cupped portions (1220) similar to cupped portions (1020). Unlike depth limiter (1010) that is shown as including four legs (1014), depth limiter (1210) includes three legs (1214). For example, legs (1214) may be circumferentially separated uniformly by approximately 120 degrees around hub (1212). However, legs (1214) may be non-uniformly separated. In some instances, the use of three or four legs (1014, 1214, 1314, 1414) may allow for further stability and ergonomics to allow for finger grip of user (U). Legs (1214) may flex similar to legs (1014) shown above with reference to FIGS. 12A-12B.

F. Sixth Exemplary Depth Limiter

FIGS. 15-17B show a sixth exemplary depth limiter (1310). Particularly, FIG. 15 shows a perspective view of depth limiter (1310). As shown, depth limiter (1310) includes a hub (1312) and a plurality of legs (1314). extending from hub (1312). Depth limiter (1310) may be used in combination with any one or more of depth limiters (200, 300) described above. While hub (1312) is shown as being generally cylindrically shaped, other shapes of hub (1312) are also envisioned. As shown, hub (1312) includes an aperture (1316) and a plurality of notches (1318). Notches (1318) may transform depth limiter (1310) from a movable configuration to a fixed configuration.

Aperture (1316) includes a gripping surface (1320) that is configured to couple with the outer surface of cannula tube (124) in the fixed configuration. Gripping surface (1320) may extend parallel to a longitudinal axis defined by cannula tube (124) of cannula (120). Gripping surface (1320) may be smooth or non-smooth. As shown in FIG. 15, gripping surface (1320) may include a smooth surface that frictionally engages ribs (128) of cannula (120) in the fixed configuration. Alternatively, gripping surface (1320) may include a non-smooth surface may include one or more features to lockingly engage cannula tube (124). Hub (1312) of depth limiter (1310) may be secured to cannula (120) with mating threads (like a nut) or may be secured to a scalloped cannula using an interference fit. Threads may be helical or non-helical (e.g., scallops). For example, gripping surface (1320) may include at least one tooth configured to lockingly engage with at least one of rib (128) of cannula (120). For example, notches (1318) may be formed in hub (1312) of depth limiter (1310), such that each leg (1314) may selectively collapse when adequate force acts on that leg (1314), causing gripping surface (1320) to clamp down tighter on cannula (120). As such, depth limiter (1310) may limit insertion depth of cannula tube (124) of cannula (120) and provide stability control of cannula tube (124) of cannula (120).

Legs (1314) may have a generally tapering cross-section moving radially away from hub (1312). For example, one or more ends of legs (1314) may include distal pad (1322) to distribute the downward force. As shown, legs (1314) are separated by approximately 90 degrees. Legs (1314) may be non-uniformly separated. Additionally, more or fewer legs (1314) are also envisioned (similar to those shown in FIGS. 13-14 associated with depth limiters (1110, 1210). Depth limiter (1310) may provide additional stability to the trocar (110) for anti-tip resistance. Depth limiter (1310) may be configured to restrict sudden tilting using legs (1314), thereby stabilizing cannula (120). Legs (1314) may contact body wall to prevent or at least decelerate tip over of cannula (120). While FIGS. 16A-17B describe depth limiter (1310) with reference to cannula tube (124) of trocar (110), other cannula tubes (e.g., cannula tube (22)) may also be used.

Figure 17A:
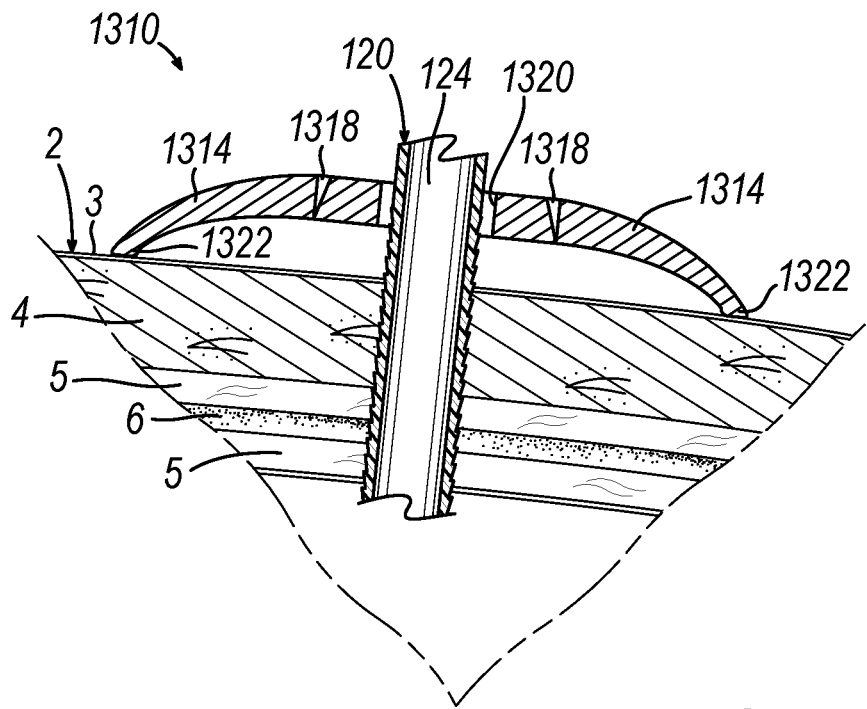
FIG. 17A depicts a partial side sectional view of the depth limiter of FIG. 15 coupled with the cannula tube of the cannula assembly of FIG. 5, where the legs of the depth limiter are in a non-deployed configuration.

FIGS. 16A and 17A show depth limiter (1310) in the movable configuration. Particularly, FIG. 16A shows a top plan view of depth limiter (1310) of FIG. 15 coupled with cannula tube (124) of cannula assembly (112) of FIG. 5, where hub (1312) of depth limiter (1310) is in a movable configuration. FIG. 17A shows a partial side sectional view of depth limiter (1310) of FIG. 15 coupled with cannula tube (124) of cannula assembly (112) of FIG. 5, where legs (1314) of depth limiter (1310) are in the movable configuration. In the movable configuration of FIGS. 16A and 17A, gripping surface (1320) forms a second effective diameter (ED2) that allows for axial movement of depth limiter (1310) relative to an outer diameter of cannula tube (124) of cannula (120). In the movable configuration, also considered the resting configuration, legs (1314) are curved downwardly. Once pushed against abdominal wall (2), legs (1314) bend flatter and provide a reaction force against abdominal wall (2) and cannula (120).

Figure 17B:
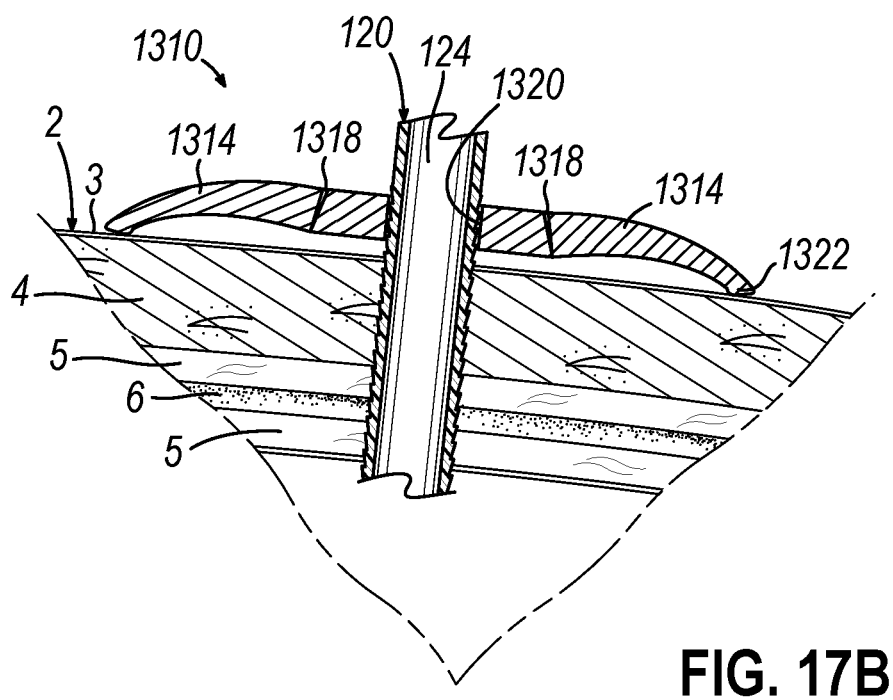
FIG. 17B depicts a partial side sectional view of the depth limiter of FIG. 15 coupled with the cannula tube of the cannula assembly of FIG. 5 following detachment and removal of the obturator, where the legs of the depth limiter are in a deployed configuration.

FIGS. 16B and 17B show depth limiter (1310) in the fixed configuration.

Particularly, FIG. 16B shows a partial side sectional view of depth limiter (1310) of FIG. 15 coupled with cannula tube (124) of cannula assembly (112) of FIG. 5 following detachment and removal of obturator (116), where legs (1314) of depth limiter (1310) are in the fixed configuration. FIG. 17B shows a partial side sectional view of depth limiter (1310) of FIG. 15 coupled with cannula tube (124) of cannula assembly (112) of FIG. 5 following detachment and removal of obturator (116), where legs (1314) of depth limiter (1310) are in the fixed configuration. In the fixed configuration, notches (1318) may be forced closed to narrow aperture (1316). Legs (1314) may reduce the amount of rotational displacement/tilt that trocar (110) may exhibit, and may also reduce the velocity at which trocar (110) may assume that tilt (i.e., preventing sudden movements within the body). In the fixed configuration, gripping surfaces (1320) collectively form a first effective diameter (ED1) that restricts axial movement of depth limiter (1310) relative to cannula (120) by directly contacting cannula (120). Depth limiter (1310) may be disposable or reusable.

G. Seventh Exemplary Depth Limiter

Figure 18:
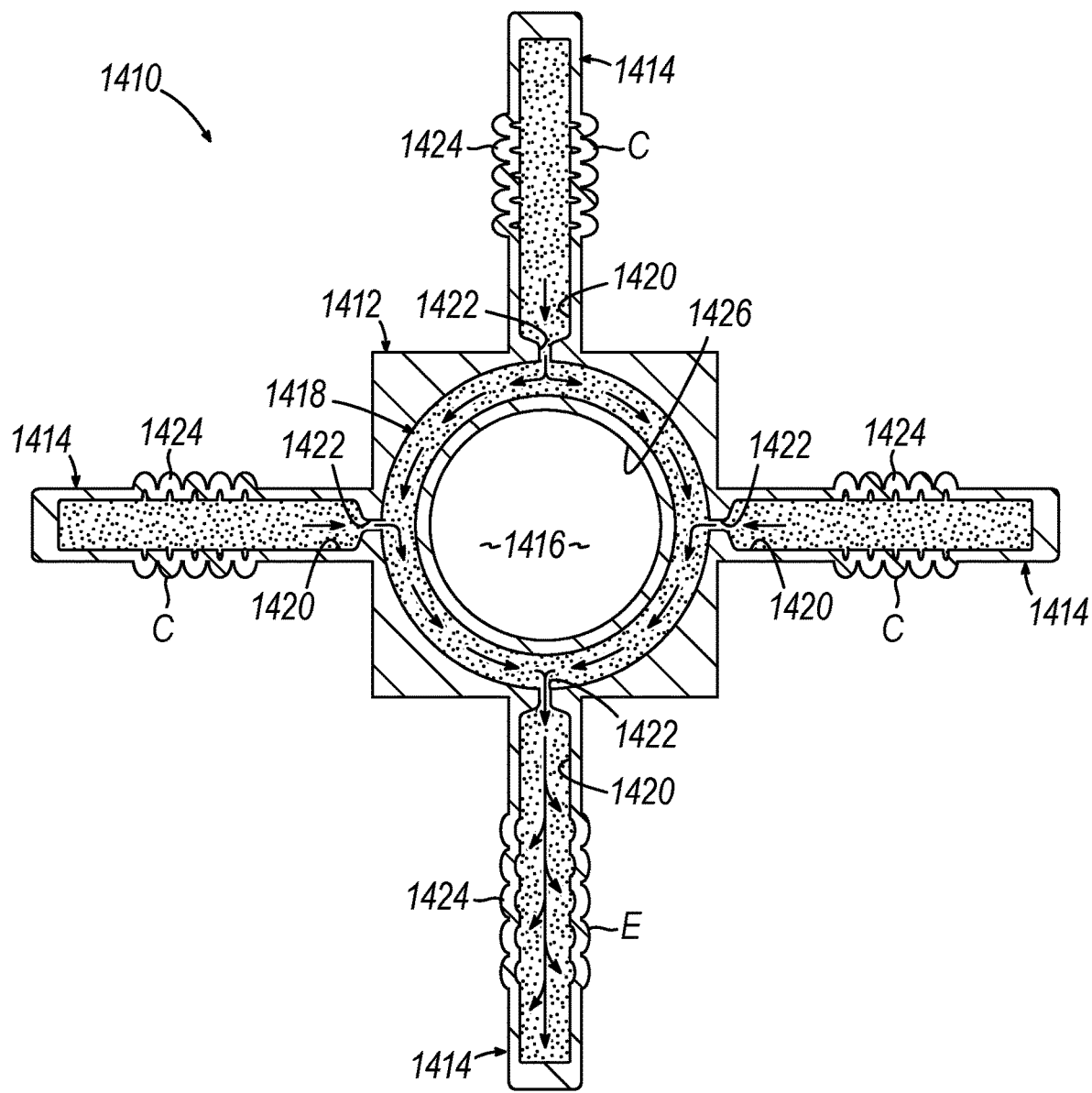
FIG. 18 depicts a top sectional view of another exemplary depth limiter that includes a fluid chamber and four legs.

FIG. 18 shows a top sectional view of a seventh exemplary depth limiter (1410). Depth limiter (1410) includes a hub (1412) and a plurality of legs (1414) extending from hub (1412). Depth limiter (1410) may be used in combination with any one or more of depth limiters (200, 300) described above. In some versions, hub (1412) may being generally cylindrically shaped. As shown, hub (1412) includes an aperture (1416) configured to receive cannula tube (124) of cannula (120). As shown, legs (1414) may be separated by approximately 90 degrees. However, legs (1414) may be non-uniformly separated. Additionally, more or fewer legs (1414) are also envisioned, similar to depth limiters (1110, 1210) shown in FIGS. 13-14.

Depth limiter (1410) includes a fluid chamber (1418) that may be disposed within hub (1412) and legs (1414). For example, fluid chamber (1418) may be completely enclosed by hub (1412) and legs (1414). Fluid chamber may include a plurality of fluid passageways (1420) that include narrow portions (1422). Narrow portions (1422) may be disposed generally between hub (1412) and legs (1414). Narrow portions (1422) regulate flow between hub (1412) and legs (1414). In other words, fluid chamber (1418) may be integrated into legs (1414) with narrow portions (1422) forming restricted areas of flow at the base of each leg (1414). As shown, one or more ends of legs (1414) may include extensive portion (1424) configured to extend from a compressed configuration (C) to an expanded configuration (E). Depth limiter (1410) may provide additional stability to the trocar (110) for anti-tip resistance. As additional tilt force acts on each independent leg (1414), the fluid may redistribute to the other legs (1414), but the fluid may be restricted by these restricted areas (1422), thus creating a damping effect on the tilting of trocar (110). This damping effect may regulate the speed at which trocar (110) tilts. As a result, depth limiter (1410) may restrict sudden tilting of trocar (110) via restricted fluid flow between legs (1414), thereby stabilizing cannula (120).

Aperture (1416) includes a gripping surface (1426) that may couple with the outer surface of cannula tube (124) of cannula (120). Gripping surface (1426) may extend parallel to a longitudinal axis defined by cannula tube (124) of cannula (120). Gripping surface (1426) may be smooth or non-smooth. As shown in FIG. 18, gripping surface (1426) may include a smooth surface that frictionally engages ribs (128) of cannula (120). Alternatively, gripping surface (1426) may include a non-smooth surface may include one or more features to lockingly engage cannula tube (124). For example, hub (1412) of depth limiter (1410) may be secured to cannula (120) using mating threads (like a nut) or secured to a scalloped cannula. Threads may be helical or non-helical (e.g., scallops). For example, gripping surface (1426) may include at least one tooth configured to lockingly engage with at least one of rib (128) of cannula (120). Depth limiter (1410) may be disposable.

III. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A depth limiter configured to couple with a first cannula tube of a first trocar having a first tube cross dimension, the depth limiter comprising: (a) an outer frame portion; and (b) an inner gripping portion housed within the outer frame portion, wherein the inner gripping portion includes a plurality of lobes flexible relative to each other between a relaxed configuration and at least one flexed configuration including a first flexed configuration, wherein in the relaxed configuration the plurality of lobes collectively form a first effective cross dimension, wherein the first effective cross dimension is configured to be less than the first tube cross dimension, wherein in the first flexed configuration the plurality of lobes collectively form a second effective cross dimension greater than the first effective cross dimension, wherein the second effective cross dimension is configured to be equal to the first tube cross dimension such that the second effective cross dimension is sized to restrict axial movement of the depth limiter relative to the first cannula tube of the first trocar.

Example 2

The depth limiter of Example 1, wherein the inner gripping portion is more flexible than the outer frame portion.

Example 3

The depth limiter of any of the preceding Examples, wherein the depth limiter is configured to couple with a second cannula tube of a second trocar having a second tube cross dimension greater than the first tube cross dimension, wherein the at least one flexed configuration includes a second flexed configuration, wherein in the second flexed configuration the plurality of lobes collectively form a third effective cross dimension greater than the second effective cross dimension, wherein the third effective cross dimension is configured to be equal to the second tube cross dimension such that the third effective cross dimension is sized to restrict axial movement of the depth limiter relative to the second cannula tube of the second trocar.

Example 4

The depth limiter of any of the preceding Examples, wherein each of the lobes is biased radially inwardly along a length thereof relative to a central axis of the depth limiter toward the relaxed configuration.

Example 5

The depth limiter of Example 4, wherein each of the lobes is flexible radially outwardly along the length thereof relative to the central axis of the depth limiter from the relaxed configuration toward the at least one flexed configuration.

Example 6

The depth limiter of any of the preceding Examples, wherein the plurality of lobes includes three lobes in a triangular arrangement about a central axis of the depth limiter.

Example 7

The depth limiter of any of the preceding Examples, wherein the lobes are interconnected via respective joints.

Example 8

The depth limiter of Example 7, wherein the outer frame portion includes a plurality of circumferentially arranged recesses, wherein the recesses receive the joints of the inner gripping portion.

Example 9

The depth limiter of any of the preceding Examples, wherein the lobes are configured to directly grip an outer surface of the first cannula tube when urged to the first flexed configuration by the first cannula tube.

Example 10

The depth limiter of any of the preceding Examples, wherein each of the lobes is spaced apart from the outer frame portion at least when the lobes are in the relaxed configuration.

Example 11

The depth limiter of any of the preceding Examples, wherein the outer frame portion comprises a proximal hub and a distal flange extending radially outwardly from the proximal hub relative to a central axis of the depth limiter.

Example 12

The depth limiter of any of the preceding Examples, wherein the inner gripping portion comprises an elastomeric material.

Example 13

The depth limiter of any of the preceding Examples, wherein the outer frame portion comprises a polymeric material.

Example 14

The depth limiter of any of the preceding Examples, wherein the outer frame portion and the inner gripping portion are integrally formed together as a unitary piece.

Example 15

The depth limiter of any of the preceding Examples, wherein the outer frame portion and the inner gripping portion are separately formed from each other as distinct pieces configured to be coupled together.

Example 16

A surgical access device assembly comprising: (a) a cannula having a cannula cross dimension, wherein the cannula includes a working channel configured to guide a surgical instrument along a central axis of the cannula; and (b) a depth limiter movably coupled with the cannula and including: (i) an outer frame portion, and (ii) an inner gripping portion housed within the outer frame portion and including a plurality of lobes flexible relative to each other between a relaxed configuration and at least one flexed configuration, wherein in the at least one flexed configuration the plurality of lobes are configured to deform and resiliently bear inwardly against the cannula to restrict axial movement of the depth limiter relative to the cannula.

Example 17

The surgical access device assembly of Example 16, wherein the outer frame portion is rigid and the inner gripping portion is flexible relative to the outer frame portion.

Example 18

The surgical access device assembly of any of Examples 16 through 17, wherein the cannula is configured to urge the plurality of lobes from the relaxed configuration toward the at least one flexed configuration.

Example 19

A method of using a depth limiter with a trocar, wherein the depth limiter includes an outer frame portion and an inner gripping portion housed within the outer frame portion and including a plurality of lobes flexible relative to each other between a relaxed configuration and at least one flexed configuration, the method comprising: (a) positioning the inner gripping portion about a cannula tube of a trocar such that the cannula tube urges the lobes from the relaxed configuration to the at least one flexed configuration; and (b) frictionally engaging the lobes with the cannula tube to thereby restrict axial movement of the depth limiter relative to the cannula tube of the trocar.

Example 20

The method of Example 19, further comprising: (a) frictionally disengaging the lobes from the cannula tube by applying a threshold force to the depth limiter; and (b) sliding the lobes axially along the cannula tube to adjust an axial position of the depth limiter relative to the cannula tube.

IV. Miscellaneous

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

Furthermore, any one or more of the teachings herein may be combined with any one or more of the teachings disclosed in U.S. patent application Ser. No. 17/213,302, entitled "Pinch-To-Release Cannula Depth Limiter," filed on Mar. 26, 2021, issued as U.S. Pat. No. 11,633,211 on Apr. 25, 2023; U.S. patent application Ser. No. 17/213,304, entitled "Multi-Diameter Cannula Depth Limiter," filed on Mar. 26, 2021, published as U.S. Pub. No. 2021/0338281 on Nov. 4, 2021; U.S. patent application Ser. No. 17/213,401, entitled "Pinch-To-Clamp Cannula Depth Limiter," filed on Mar. 26, 2021, published as U.S. Pub. No. 2021/0338273 on Nov. 4, 2021; U.S. patent application Ser. No. 17/213,415, entitled "Threaded Cannula Depth Limiter," filed on Mar. 26, 2021, published as U.S. Pub. No. 2021/0338274 on Nov. 4, 2021; U.S. patent application Ser. No. 17/213,426, entitled "Tilting Tang Cannula Depth Limiter," filed on Mar. 26, 2021 issued as U.S. Pat. No. 11 712,297 on Aug. 1, 2023; U.S. patent application Ser. No. 17/231,431, entitled "Two Piece Separable Obturator," filed on, Mar. 26, 2021, published as U.S. Pub. No. 2021/0338275 on Nov. 4, 2021; U.S. patent application Ser. No. 17/213,434, entitled "Latchless Obturator with Interference Fit Feature," filed on Mar. 26, 2021, published as U.S. Pub. No. 2021/0338269 on Nov. 4, 2021; U.S. patent application Ser. No. 17/213,437, entitled "Balancing Feature for Reusable Trocar," filed on, Mar. 26, 2021, issued as U.S. Pat. No. 11,559,329 on Jan. 24, 2021; U.S. patent application Ser. No. 17/213,508, entitled "Airflow Channels and Patterns in Lumen for Cannula," filed on Mar. 26, 2021, published as U.S. Pub. No. 2021/0338278 on Nov. 4, 2021; and/or U.S. patent application Ser. No. 17/213,518, entitled "Stabilizer for Surgical Shafts or Cannulas," filed on Mar. 26, 2021, published as U.S. Pub. No. 2021/0338371 on Nov. 4, 2021. The disclosure of each of these patent applications is incorporated by reference herein.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, California Similarly, those of ordinary skill in the art will recognize that various teachings herein may be readily combined with various teachings of any of the following: U.S. Pat. No. 5,792,135, entitled "Articulated Surgical Instrument For Performing Minimally Invasive Surgery With Enhanced Dexterity and Sensitivity," issued Aug. 11, 1998, the disclosure of which is incorporated by reference herein; U.S. Pat. No. 8,783,541, entitled "Robotically-Controlled Surgical End Effector System," issued Jul. 22, 2014, the disclosure of which is incorporated by reference herein; U.S. Pat. No. 8,479,969, entitled "Drive Interface for Operably Coupling a Manipulatable Surgical Tool to a Robot," issued Jul. 9, 2013; U.S. Pat. No. 8,800,838, entitled "Robotically-Controlled Cable-Based Surgical End Effectors," issued Aug. 12, 2014, the disclosure of which is incorporated by reference herein; and/or U.S. Pat. No. 8,573,465, entitled "Robotically-Controlled Surgical End Effector System with Rotary Actuated Closure Systems," issued Nov. 5, 2013, the disclosure of which is incorporated by reference herein.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

I claim:

1. A depth limiter configured to couple with a first cannula tube of a first trocar having a first tube cross dimension, the depth limiter comprising:
    (a) an outer frame portion; and
    (b) an inner gripping portion housed within the outer frame portion, wherein the inner gripping portion includes a plurality of lobes flexible relative to each other between a relaxed configuration and at least one flexed configuration including a first flexed configuration,
    wherein in the relaxed configuration the plurality of lobes collectively form a first effective cross dimension, wherein the first effective cross dimension is configured to be less than the first tube cross dimension,
    wherein in the first flexed configuration the plurality of lobes collectively form a second effective cross dimension greater than the first effective cross dimension, wherein the second effective cross dimension is configured to be equal to the first tube cross dimension such that the second effective cross dimension is sized to restrict axial movement of the depth limiter relative to the first cannula tube of the first trocar,
    wherein the outer frame portion comprises a proximal hub and a distal flange extending radially outwardly from the proximal hub relative to a central axis of the depth limiter, wherein the distal flange defines a distalmost and radially outermost portion of the depth limiter.

2. The depth limiter of claim 1, wherein the inner gripping portion is more flexible than the outer frame portion.

3. The depth limiter of claim 1, wherein the depth limiter is configured to couple with a second cannula tube of a second trocar having a second tube cross dimension greater than the first tube cross dimension, wherein the at least one flexed configuration includes a second flexed configuration, wherein in the second flexed configuration the plurality of lobes collectively form a third effective cross dimension greater than the second effective cross dimension, wherein the third effective cross dimension is configured to be equal to the second tube cross dimension such that the third effective cross dimension is sized to restrict axial movement of the depth limiter relative to the second cannula tube of the second trocar.

4. The depth limiter of claim 1, wherein each of the lobes is biased radially inwardly along a length thereof relative to a central axis of the depth limiter toward the relaxed configuration.

5. The depth limiter of claim 4, wherein each of the lobes is flexible radially outwardly along the length thereof relative to the central axis of the depth limiter from the relaxed configuration toward the at least one flexed configuration.

6. The depth limiter of claim 1, wherein the plurality of lobes includes three lobes in a triangular arrangement about a central axis of the depth limiter.

7. The depth limiter of claim 1, wherein the lobes are interconnected via respective joints.

8. The depth limiter of claim 7, wherein the outer frame portion includes a plurality of circumferentially arranged recesses, wherein the recesses receive the joints of the inner gripping portion.

9. The depth limiter of claim 1, wherein the lobes are configured to directly grip an outer surface of the first cannula tube when urged to the first flexed configuration by the first cannula tube.

10. The depth limiter of claim 1, wherein each of the lobes is spaced apart from the outer frame portion at least when the lobes are in the relaxed configuration.

11. The depth limiter of claim 1, wherein the inner gripping portion comprises an elastomeric material.

12. The depth limiter of claim 1, wherein the outer frame portion comprises a polymeric material.

13. The depth limiter of claim 1, wherein the outer frame portion and the inner gripping portion are integrally formed together as a unitary piece.

14. The depth limiter of claim 1, wherein the outer frame portion and the inner gripping portion are separately formed from each other as distinct pieces configured to be coupled together.

15. The depth limiter of claim 1, wherein the proximal hub is cylindrical.

16. A depth limiter configured to couple with a cannula tube of a trocar having a tube cross dimension, the depth limiter comprising:
(a) an outer frame portion including:
 (i) a proximal hub having a plurality of proximally-facing recesses circumferentially spaced uniformly about the proximal hub, wherein the proximal hub defines a cylindrical bore extending along a central axis of the depth limiter, and
 (ii) a distal flange extending radially outwardly from the proximal hub; and
(b) an inner gripping portion housed within the outer frame portion, wherein the inner gripping portion includes:
 (i) a plurality of lobes flexible relative to each other between a relaxed configuration and a flexed configuration, wherein each lobe of the plurality of lobes is flexibly received within the cylindrical bore of the proximal hub, and
 (ii) a plurality of joints, wherein each joint of the plurality of joints interconnects a corresponding pair of lobes of the plurality of lobes, wherein each joint of the plurality of joints is fixedly received within a corresponding proximally-facing recess of the plurality of proximally-facing recesses,
wherein in the relaxed configuration the plurality of lobes collectively form a first effective cross dimension, wherein the first effective cross dimension is configured to be less than the tube cross dimension,
wherein in the flexed configuration the plurality of lobes collectively form a second effective cross dimension greater than the first effective cross dimension, wherein the second effective cross dimension is configured to be equal to the tube cross dimension such that the second effective cross dimension is sized to restrict axial movement of the depth limiter relative to the cannula tube of the trocar,
wherein the inner gripping portion is more flexible than the outer frame portion,
wherein each of the lobes is biased radially inwardly along a length thereof relative to the central axis of the depth limiter toward the relaxed configuration.

17. The depth limiter of claim 16, wherein each of the lobes is flexible radially outwardly along the length thereof relative to the central axis of the depth limiter from the relaxed configuration toward the flexed configuration.

18. The depth limiter of claim 16, wherein the inner gripping portion comprises an elastomeric material, wherein the outer frame portion comprises a polymeric material.

19. A depth limiter configured to couple with a cannula tube of a trocar having a tube cross dimension, the depth limiter comprising:
(a) an outer frame portion; and
(b) an inner gripping portion housed within the outer frame portion, wherein the inner gripping portion includes a plurality of lobes flexible relative to each other between a relaxed configuration and a flexed configuration,
wherein in the relaxed configuration the plurality of lobes collectively form a first effective cross dimension, wherein the first effective cross dimension is configured to be less than the tube cross dimension,
wherein in the flexed configuration the plurality of lobes collectively form a second effective cross dimension greater than the first effective cross dimension, wherein the second effective cross dimension is configured to be equal to the tube cross dimension such that the second effective cross dimension is sized to restrict axial movement of the depth limiter relative to the cannula tube of the trocar,
wherein the plurality of lobes includes three lobes in a triangular arrangement about a central axis of the depth limiter such that the three lobes collectively define an expandable triangular bore extending longitudinally along the central axis of the depth limiter, and
wherein the lobes are interconnected via respective joints.

20. The depth limiter of claim 19, wherein the outer frame portion includes a plurality of circumferentially arranged recesses, wherein the recesses receive the joints of the inner gripping portion.

\* \* \* \* \*